US011727771B2

(12) United States Patent
Olsen

(10) Patent No.: US 11,727,771 B2
(45) Date of Patent: Aug. 15, 2023

(54) TAMPER-RESISTANT WEARABLE CARETAKING DEVICE

(71) Applicant: GREGORY D. OLSEN, DDS, MSD, LLC, Queen Creek, AZ (US)

(72) Inventor: Gregory David Olsen, Queen Creek, AZ (US)

(73) Assignee: Gregory D. Olsen, DDS, MSD, LLC, Queen Creek, AZ (US)

( * ) Notice: Subject to any disclaimer, the term of this patent is extended or adjusted under 35 U.S.C. 154(b) by 0 days.

(21) Appl. No.: 17/484,663

(22) Filed: Sep. 24, 2021

(65) Prior Publication Data
US 2022/0101702 A1 Mar. 31, 2022

Related U.S. Application Data

(60) Provisional application No. 63/083,699, filed on Sep. 25, 2020.

(51) Int. Cl.
*G08B 13/06* (2006.01)
*G08B 25/01* (2006.01)
(Continued)

(52) U.S. Cl.
CPC ............ *G08B 13/06* (2013.01); *A44C 5/0061* (2013.01); *A44C 5/145* (2013.01); *A61B 5/0205* (2013.01);
(Continued)

(58) Field of Classification Search
CPC .... G08B 13/06; G08B 25/016; A44C 5/0061; A44C 5/145; A61B 5/0205; A61B 5/681;
(Continued)

(56) References Cited

U.S. PATENT DOCUMENTS

2013/0182382 A1* 7/2013 Vardi ................. G08B 21/0492
361/679.01
2015/0187190 A1* 7/2015 Fugate .................. G08B 21/24
340/8.1
(Continued)

OTHER PUBLICATIONS

The International Searching Authority, "Search Report" in Application No. PCT/US21/52082, dated Dec. 23, 2021 18 pages.

*Primary Examiner* — Omar Casillashernandez
(74) *Attorney, Agent, or Firm* — Hickman Becker Bingham Ledesma LLP

(57) ABSTRACT

Techniques are described herein for a wearable device that is configured to prevent unauthorized removal and to facilitate detection of unauthorized removal attempts or tampering with a band of the device. The wearable device includes one or more circuit systems, each of which is configured to conduct an electric current. Attempts to remove the device cause components of one or more of the circuit systems to break/fail, which disrupts the electric currents of the broken circuit systems. Such electric current disruptions are detected by the wearable device as evidence of an unauthorized removal attempt or tampering with the device band. The wearable device may include a hook-based latching mechanism or a rod-based latching mechanism. According to various embodiments, the wearable device is engaged with or disengaged from around a limb of a wearer responsive to an engage or disengage instruction from an authorized user of a client device.

19 Claims, 18 Drawing Sheets

(51) Int. Cl.
    *A44C 5/14* (2006.01)
    *G06F 1/16* (2006.01)
    *A61B 5/0205* (2006.01)
    *A61B 5/00* (2006.01)
    *A44C 5/00* (2006.01)

(52) U.S. Cl.
    CPC .............. *A61B 5/681* (2013.01); *G06F 1/163* (2013.01); *G08B 25/016* (2013.01)

(58) Field of Classification Search
    CPC . A61B 5/02438; A61B 5/1112; A61B 5/1118; A61B 2505/07; A61B 2560/0276; A61B 5/14542; A61B 5/4833; A61B 5/6831; A61B 5/6843; A61B 5/6844; G06F 1/163; G06F 21/86
    USPC ........................................................ 340/542
    See application file for complete search history.

(56)  References Cited

U.S. PATENT DOCUMENTS

| | | | |
|---|---|---|---|
| 2016/0078752 A1* | 3/2016 | Vardi .................... | H04B 1/385 |
| | | | 340/506 |
| 2020/0205678 A1* | 7/2020 | Kawabata ........... | A61B 5/02116 |
| 2020/0250953 A1* | 8/2020 | Wojcik .................. | G08B 21/22 |
| 2022/0143483 A1* | 5/2022 | Liu ......................... | G06F 1/163 |
| 2022/0252368 A1* | 8/2022 | Dugo ..................... | F41A 19/64 |

* cited by examiner

| | LOCATION 1120 | DAYS 1122 | TIMES 1124 | EXCEPTIONS 1126 | GROUP 1128 |
|---|---|---|---|---|---|
| 1102 | ZONE 1024 | M-F | 8 AM - 3 PM | Oct. 15, 2021; Dec. 18, 2021 - Jan. 4, 2022; | "SCHOOL DAY" |
| 1104 | ZONE 1022 | M-F | 3:30 PM - 7:30 AM | | "SCHOOL DAY" |
| 1106 | ZONE 1022 | Sa-Su | ALL | | "WEEKEND" |
| 1108 | ZONE 1026 | ALL | ALL | | "PARK" |
| 1110 | NO ALERT | Oct. 2, 2021 | ALL | | "FATHER" |
| 1112 | NO ALERT | M-F | 7:30 AM - 8 AM; 3 PM - 3:30 PM | | "SCHOOL DAY" |
| 1114 | USER A, 20 FT | ALL | ALL | | "MOTHER" |
| 1116 | USER B, 10 FT | FIRST WEEKEND OF EVERY MONTH | ALL | | "FATHER" |
| 1118 | ZONE 1028 | FIRST WEEKEND OF EVERY MONTH | ALL | | "FATHER" |

FIG. 11

TAMPER-RESISTANT WEARABLE CARETAKING DEVICE

BENEFIT CLAIM

This application claims the benefit of Provisional Application 63/083,699, filed Sep. 25, 2020, the entire contents of which is hereby incorporated by reference as if fully set forth herein, under 35 U.S.C. § 119(e).

FIELD OF THE INVENTION

The present invention relates to a wearable device, and more specifically, to a wearable device that detects information regarding a wearer and that facilitates detection of tampering or unauthorized device removal.

BACKGROUND

It can be very difficult for a caretaker to track the locations and well-being of individuals (referred to herein as "care recipients") in their care. It is not always possible for a caretaker to be in the same space as care recipients, or to closely monitor the care recipients. For example, the care recipient may be in a different space than the caretaker (such as when the care recipient is a child at school or at a friend's house), the caretaker and care recipient may be in a large and/or busy space (such as in a store, or a busy park), or the caretaker may need to perform a task that requires diverting their attention from the care recipient.

There are some devices that aid caretakers with caretaking tasks. For example, monitors (such as vital sign monitors, audio monitors, and/or video monitors) may be used to allow a caretaker to remotely monitor a care recipient. However, many such monitors are only practical to use in limited circumstances. Consequently, the monitors are not able to aid with caretaking in many situations, especially when the care recipient is in a space that is not under the control of the caretaker (such as at a park, a school, or a store, etc.).

Some monitors are wearable monitors that are able to track location and/or vital signs of a care recipient and, at times, allow communication with another device. Such monitors may be configured to generate alerts when unusual or unexpected activity is detected. When a care recipient wears a wearable monitor, a caretaker may receive information about the location and/or well-being of the care recipient regardless of the location of the care recipient with respect to the caretaker. However, such monitors are easily detached from the care recipient. For example, the monitor may be detached by accident, by the care recipient, or, potentially, by another individual.

Some monitors generate alerts when detached from the care recipient, but such alerts do not prevent detachment of the wearable monitor from the care recipient. Furthermore, alarms that are keyed on detachment of a monitoring device may be initiated too late to trigger corrective action. By the time a detachment alarm is received by the caregiver, the care recipient may have already created a dangerous situation.

Thus, it would be beneficial to provide a wearable device, e.g., with care recipient monitoring capabilities, that is configured to detect conditions that precede unauthorized removal, and thereby allow corrective actions to be taken with sufficient time to prevent unauthorized removal of the monitoring device.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

BRIEF DESCRIPTION OF THE DRAWINGS

In the drawings:

FIG. 11 depicts an example set of alert rules for a wearable device.

DETAILED DESCRIPTION

Figure 1:
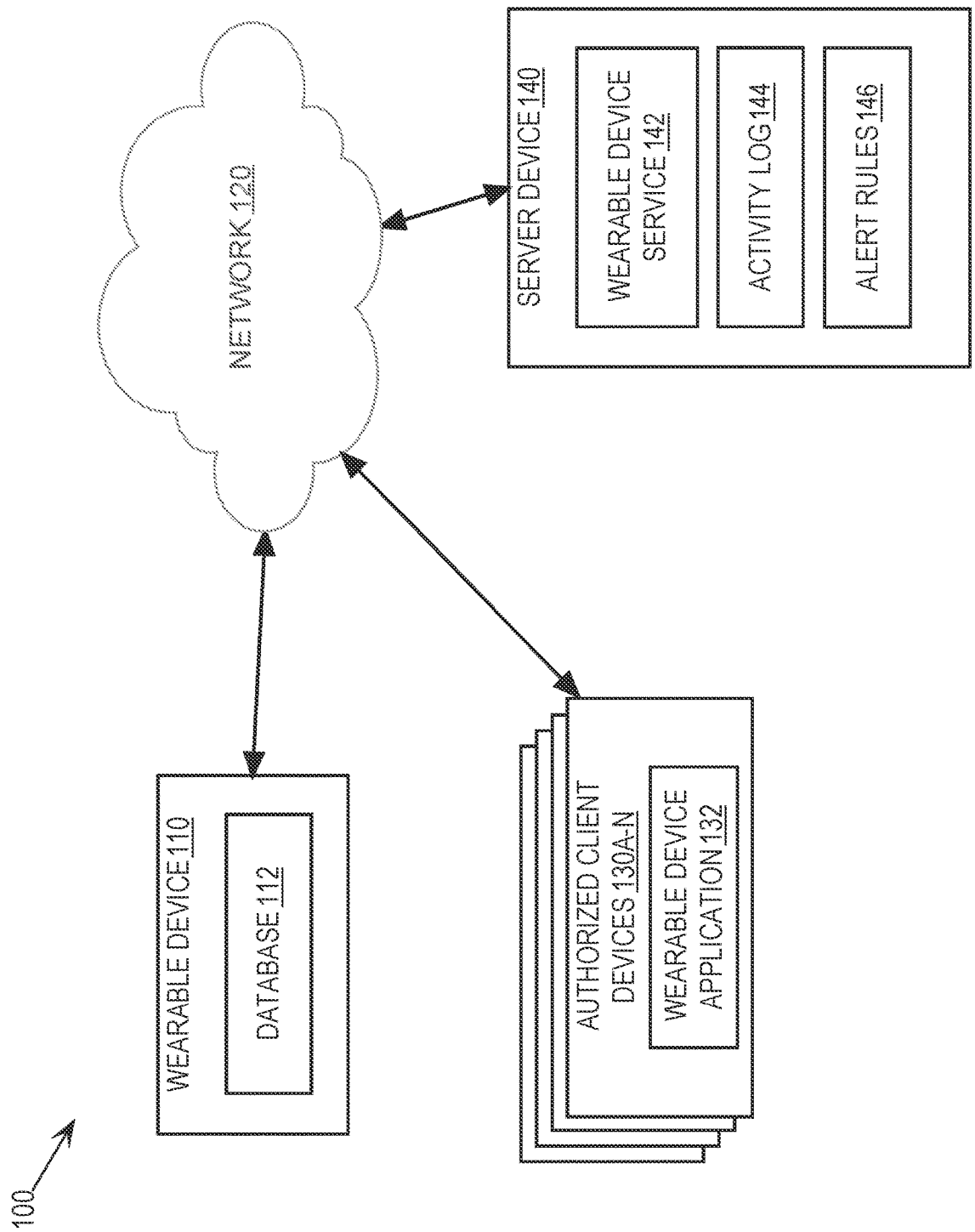
FIG. 1 depicts an example network arrangement, including a wearable device that is communicatively connected, via a communication mechanism, to one or more client devices and to a server device.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

1. General Overview

Techniques are described herein for a wearable device that is configured to prevent unauthorized removal and to facilitate detection of unauthorized removal attempts or tampering with a band of the device. For example, a wearable device is attached to a limb of a wearer by a band. The wearable device is configured to detect, before the band is detached from the limb, instances of tampering with the band. The wearable device sends information regarding detected tampering to a destination application, such as to a client application on a client device or to a service application that records such information in a device log. When the wearable device is a caretaking device used by a caretaker to aid in monitoring a care recipient, information about instances of tampering with the device (which may not result in removal of the device and ma not be apparent based on a visual inspection of the device) can be useful.

In order to detect unauthorized removal attempts and/or tampering with a band of the device, the wearable device includes a plurality of circuit systems that span the length of the band, each of which is configured to conduct an electric current. Attempts to remove the device cause components of one or more of the circuit systems to break/fail, which disrupts the electric currents of the broken circuit systems. Such electric current disruptions are detected by the wearable device as evidence of an unauthorized removal attempt or tampering with the device band.

According to various embodiments, the wearable device includes, in a body of the device, a hook-based latching mechanism that engages with the band to secure the wearable device to a limb of a wearer. The hook-based latching mechanism engages with the band by rotating a cross-bar of the mechanism, which has hook members affixed thereto. The rotation of the cross-bar causes the hook members to hook onto loops in the band, engaging the body of the device with the band of the device. When engaged, the hooks contact conductive members running the length of the band, which are also conductively connected with the hook members in the body of the device. Thus, when engaged, the hook members complete electrical circuit systems that run through the length of the device.

According to various embodiments, the wearable device includes, in a body of the device, a rod-based latching mechanism, which engages with the band to secure the wearable device to a limb of a wearer. The rod-based latching mechanism engages with the band when a rotatable cross-bar within the body of the device moves rods of the latching mechanism into a set of holes in the band. Each hole of the set of holes exposes a conductive member that runs the length of the band, which is also conductively connected to a corresponding conductive resting plate in the body of the device. When engaged, the rods rest on the conductive resting plates and also contact the conductive members through the set of holes. Thus, when engaged, the rods complete electrical circuit systems that run through the length of the device.

According to various embodiments, the wearable device is engaged with or disengaged from around a limb of a wearer responsive to an engage or disengage instruction from an authorized user. By detecting disruption of the one or more circuit systems within the wearable device while the device is engaged around the limb of a wearer, the wearable device can further detect unauthorized removal of the device from the wearer that is not performed in response to an authorized disengage instruction.

According to various embodiments, the wearable device includes one or more sensors to detect one or more attributes of a wearer, such as location and/or vital signs. The wearable device stores in storage maintained in the device, or transmits to a destination application, the detected attributes of the wearer. Having access to these detected attributes allows a caretaker to monitor the status of a care recipient wearing the wearable device. According to various embodiments, the wearable device further provides one- or two-way communication functionality to allow for communication between the care recipient and a caretaker, which further facilitates monitoring of the care recipient.

According to various embodiments, the wearable device is configured to disseminate alerts based on detected tampering, based on unauthorized device removal, or based on attributes of a wearer satisfying one or more alert rules. These alert rules may be established by a caretaker via a client application. Dissemination of an alert may involve sending alert information to one or more client devices via an installed client application, to a service application that maintains a log for the device, and/or to one or more third parties which may include local authorities or medical services. An alert rule may be tied to one or more geographic zones associated with a schedule, deviation from which causes alert dissemination. Furthermore, alert dissemination may be performed in connection with an emergency protocol that is initiated based on one or more emergency indicators, such as manually triggering the emergency protocol from the wearable device, manually triggering the emergency protocol from a client application, detecting deviation of one or more vital sign statistics recorded for the wearer from an identified healthy range of values, detecting that a location of a wearable device engaged on a limb of a wearer is outside a particular indicated zone (such as outside of a city of residence), etc.

2. Example Network Configuration

FIG. 1 depicts an example network arrangement 100 that includes a wearable device 110 that is communicatively connected, via a network 120, to one or more client devices 130A-N and to a server device 140. Wearable device 110 may be implemented by any type of computing device that is wearable and configured to send/receive communication data via a network. Network 120 may be implemented by any mechanism that facilitates the exchange of data (e.g., via the Internet) between computing devices, such as a cellular service or a wireless network, etc. Client devices 130A-N represents any number of client devices, which may be implemented by any device capable of running a wearable device (WD) application 132 and of receiving communication data via a network. Furthermore, server device 140 may be implemented by any type of computing device configured to run a wearable device (WD) service 142 and maintain an activity log 144 based on communication data received via network 120.

According to various embodiments, wearable device 110 maintains a database 112, which may be implemented by any kind of database, including a relational database, a flat text database, an XML database, etc. According to various embodiments, wearable device 110 stores information for detected instances of tampering and unauthorized removal in database 112.

Authorized client devices 130A-N run WD application 132. A particular client device 130 may be authorized to perform one or more actions relating to wearable device 110 (including one or more of configure wearable device 110, access information from wearable device 110, and/or engage or disengage wearable device 110). A client device 130 may be authorized to perform one or more actions relating to wearable device 110 in any way, such as using authentication information or encryption for communications from a WD application 132 into which an authorized user has successfully authenticated. For example, each authorized client device 130A-N, which is authorized to perform one or more actions relating to wearable device 110, have a shared secret with wearable device 110 that is used to authenticate communications from WD application 132 to wearable device 110 and to WD service 142. In this example, wearable device 110 and WD service 142 determine whether a communication is from an authorized source based on the shared secret.

3. Anti-Tampering Features

Wearable device 110 is configured to prevent unauthorized removal and to facilitate detection of unauthorized removal attempts or tampering with a band of the device while the device is engaged around a limb of a wearer. Furthermore, the band and/or body of the device may be reinforced, e.g., with continuous durable metal components, to protect the computing components and any sensor components, and to resist unauthorized removal of the device. For example, according to various embodiments, the body of wearable device 110 comprises a steel encasement enclosing any sensors (such as a vital sign sensor, a GPS locator, etc. described in detail below) and computing components of wearable device 110 to provide extra strength and resistance to destruction. Furthermore, conductive members running the length of the band may be comprised of, or reinforced with, durable metal to strengthen the band.

Once a latching mechanism that securely attaches a body of wearable device 110 to the band is engaged, each of one or more circuit systems running the length of the device comprises a closed electrical circuit, the breaking of which (if not performed by an authorized disengagement procedure) allows wearable device 110 to detect tampering and/or unauthorized removal of the device, which may cause an alert to be disseminated or the emergency protocol to be initialized.

According to various embodiments, there are multiple positions along a band of wearable device 110 (e.g., along a portion of the band that is farthest from a second portion of the band that is fixed to a body of the device) where the latching mechanism in the body of the device can engage with the band, which allows for growth of the wearer's limb.

3.1. Authorized Engaging and Disengaging

According to various embodiments, wearable device 110 is engaged with or disengaged from around a limb of a wearer responsive to an authorized engage or disengage instruction from WD application 132. According to various embodiments, engagement and disengagement of wearable device 110 may only be performed by a user that has permission to perform engagement or disengagement, and who has successfully authenticated with WD application 132. To illustrate, an authenticated user of an authorized client device 130 may send an authorized engage or disengage instruction to wearable device 110 via WD application 132, which causes wearable device 110 to engage or disengage based, at least in part, on the instruction being authorized.

Engaging wearable device 110 comprises causing the latching mechanism of the device to engage with the band of the device to fasten the device to a wearer, e.g., around the wrist or ankle. Disengaging wearable device 110 comprises causing the latching mechanism of the device to disengage with the band of the device, which allows removal of the device from the wearer.

According to various embodiments, the latching mechanism of wearable device 110 will only disengage when the device is physically docked via a physical connection to an authorized client device 130. For example, authorized client device 130A (on which a user that is authorized to engage or disengage wearable device 110 has authenticated) physically connects with wearable device 110, e.g., using a USB cable that connects to a port of client device 130A and to a port on wearable device 110. Via the physical connection, WD application 132 on client device 130A sends an engage or disengage instruction to wearable device 110. Based on the authenticated user being authorized to perform the instructed action and based on the instruction being received via a physical connection, wearable device 110 performs the instructed action, i.e., engagement or disengagement. According to various embodiments, such an instruction may be accepted via a peer-to-peer wireless connection, such as a Bluetooth connection.

According to various embodiments, a client device 130 may send an engage or disengage instruction to wearable device via network 120. For example, when sending an instruction to engage or disengage wearable device via network 120, WD application 132 provides authentication information that allows wearable device 110 to verify that the instruction is from an authentic source. For example, WD application 132 generates a message authentication code (such as an HMAC) based on the instruction information and a shared secret known to both WD application 132 and wearable device 110 (e.g., provided by a user to both devices) and sends the message authentication code with the instruction to wearable device 110. Wearable device 110 authenticates the instruction by generating a message authentication code using the shared secret and the instruction information, and determines that the source is authentic if the generated message authentication code matches the received message authentication code. Based on the authenticated user being authorized to perform the instructed action and based on the instruction being determined to be from an authentic source, wearable device 110 performs the instructed action, i.e., engagement or disengagement.

According to various embodiments, authorized engagement or disengagement of wearable device 110 causes an alert to be disseminated to at least WD service 142, which stores information for the engagement or disengagement action to activity log 144. In this way, records of engagements and disengagements of wearable device 110 are maintained in activity log 144, and WD service 142 has information regarding time periods during which wearable device 110 is engaged on a wearer. The alert information may also be sent to one or more of client devices 130A-N.

3.2. Tampering Detection

According to various embodiments, when a latching mechanism of wearable device 110 is engaged with the band, the device comprises multiple circuit systems that conduct electrical currents. Specifically, as described in further detail below, for each circuit system, one or more conductive members in the latching mechanism connect two ends of a conductive member (e.g., comprising one or more conductive plates and/or wires) running the length of the band when the latching mechanism engages with the band.

The multiple circuit systems in wearable device 110 may be broken or shorted independently, such as during an unauthorized attempt to remove wearable device 110 from the wearer. Such an unauthorized attempt may not result in removal of the device, and may not be detectable from the appearance of the device. One or more processors within wearable device 110 are configured to detect loss of current in any of the circuit systems within the device, which allows for the device to detect potential instances of tampering with the device.

To illustrate, less than till circuit systems lose electric current (either temporarily or permanently) while the latching mechanism of wearable device 110 is engaged. The absence of a constant signal from all circuit systems is detected by the one or more processors of wearable device 110. In response to detecting the temporary or permanent loss of electric current in one or more of the circuit systems, information regarding the loss of electric current in the one or more circuit systems is transmitted, via network 120, to a destination application. For example, wearable device 110 disseminates an alert in response to detecting the temporary or permanent loss of electric current in one or more of the circuit systems. The alert information for the alert may include information identifying which of the circuit systems was disabled, a number of circuit systems that were disabled, day/time information, location information, etc.

According to various embodiments, the alert information is first transmitted to WD service 142. If a particular circuit system identified in the alert information is not flagged as "ignore", WD service 142 records the alert in activity log 144 and also sets an "ignore" flag maintained in activity log 144 for the particular circuit system. WD service 142 also causes the alert information to be sent to any of client devices 130A-N that are configured to receive such alerts. If the particular circuit system identified in the alert information is flagged as "ignore"; WD service 142 either ignores the alert for that particular circuit system, or records the alert information in activity log 144, and does not send alert information to any of client devices 130A-N. A user may clear or set the "ignore" flag for a circuit system via WD application 132. Furthermore, The emergency protocol may also be initiated based on wearable device 110 detecting the loss/inconsistent signal from one or more circuit systems of the device.

3.3. Hook-Based Latching Mechanism

According to various embodiments, wearable device 110 includes, in a body of the device, a hook-based latching mechanism that engages with the band to secure the wearable device to a limb of a wearer. When engaged, the hook-based latching mechanism closes one or more circuit systems within wearable device 110. Specifically, the hook-based latching mechanism comprises one or more hooks designed to grip a band loop, which holds each hook in contact with a corresponding conductive member (such as one or more corrugated plates and/or wires) running the length of the band. Because the conductive member is connected, at the other end, to the hook, maintaining the hook in contact with the conductive member using the loop allows an electric current to be conducted through the conductive member such that the hook and the conductive member form a circuit system.

Figure 2A:
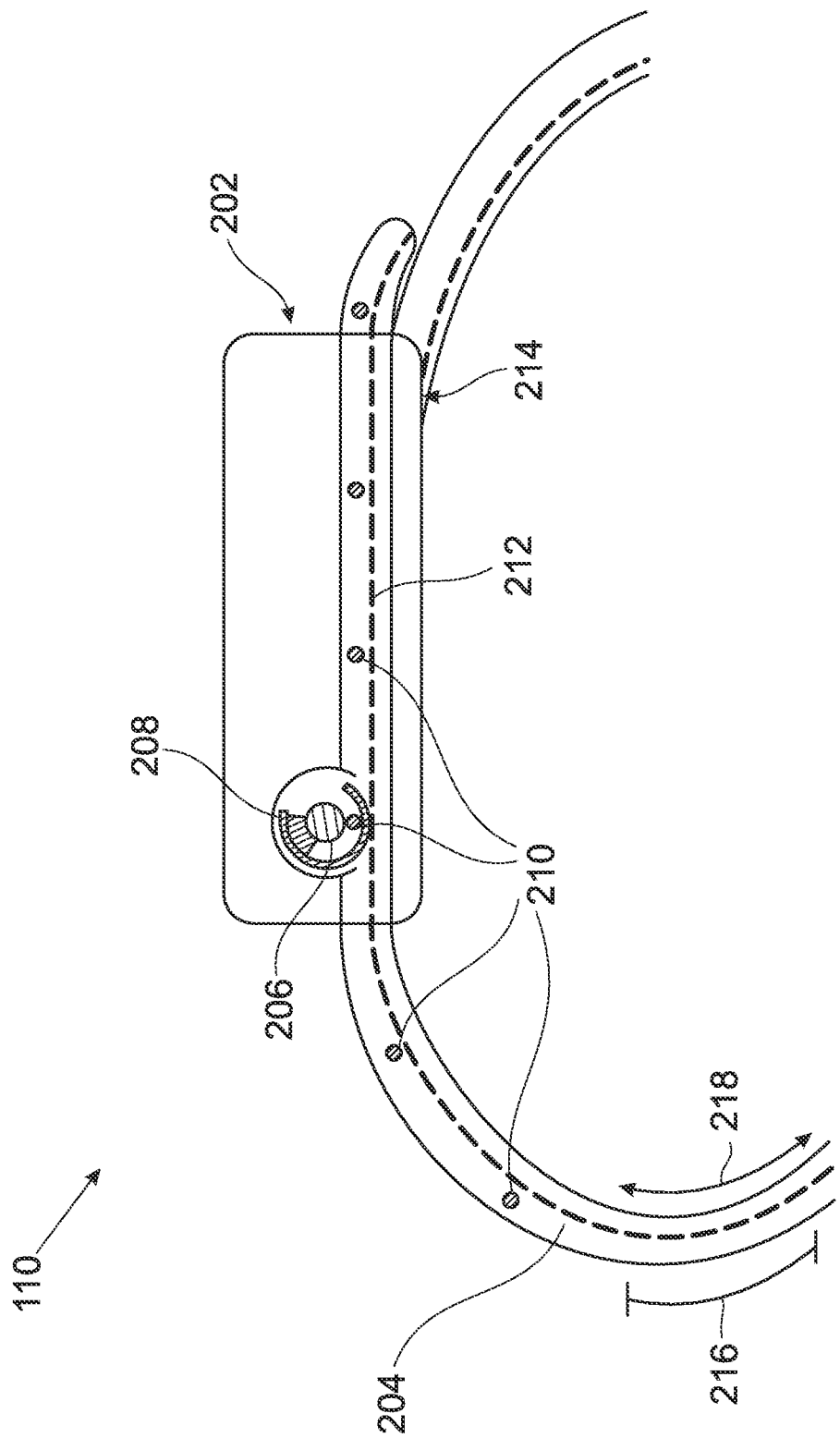
FIGS. 2A-2B depict example cross-sections of a wearable device comprising a hook-based latching mechanism that secures a body of the device to a band of the device.
Figure 2B:
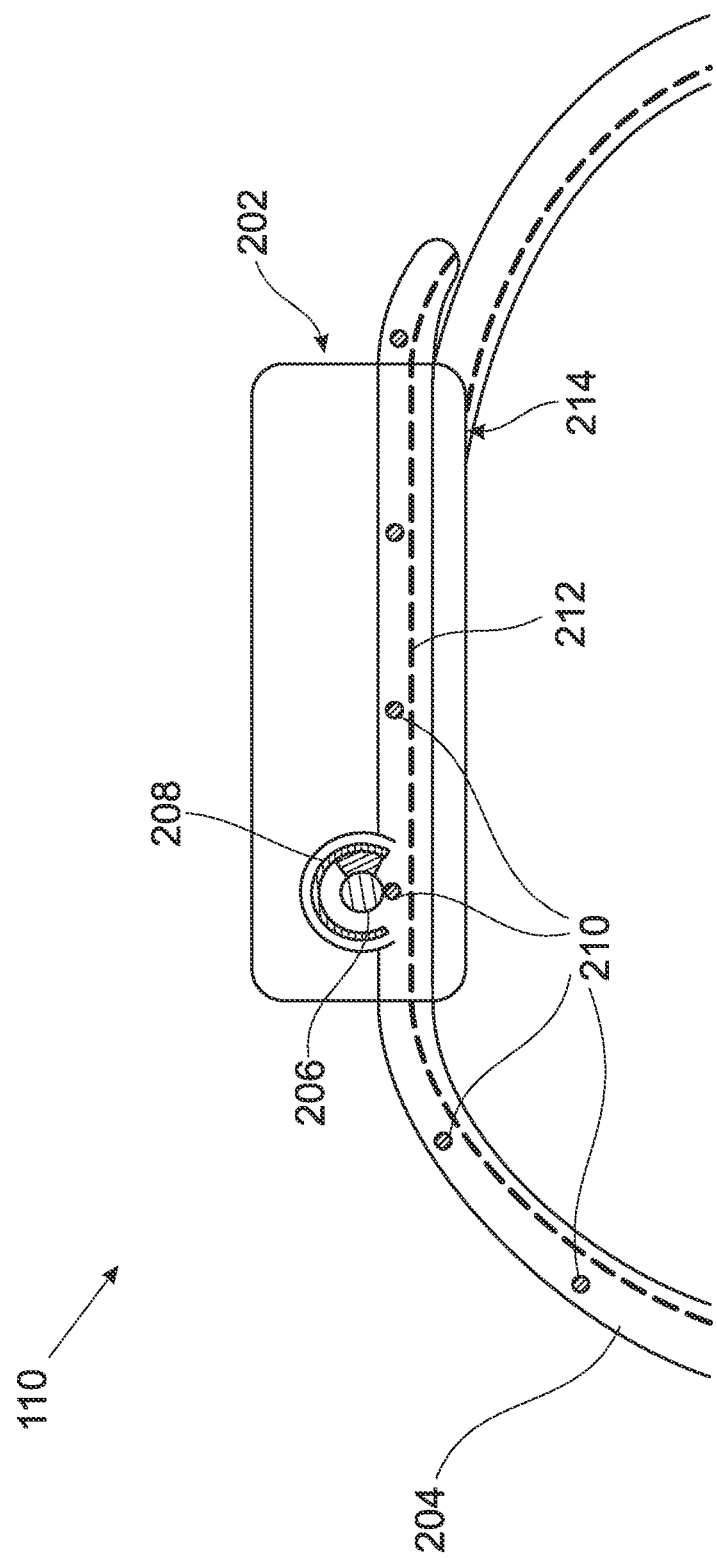

To illustrate, FIGS. 2A-2B depict example cross-sections of wearable device 110, which identify a body 202, a band 204, and a hook-based latching mechanism that secures body 202 to band 204. The hook-based latching mechanism includes a cross-bar 206 and one or more hook members 208 that are rigidly connected to cross-bar 206. According to various embodiments, hook members 208 are metal semicircles with a gauge of 0.3 mm to 0.5 mm. Hook members 208 engage band 204 via loops 210 (described in further detail below), securing the free end of the band to the body of the device. Cross-bar 206 and hook members 208 rotate together when the latch mechanism engages and disengages.

Figure 3:
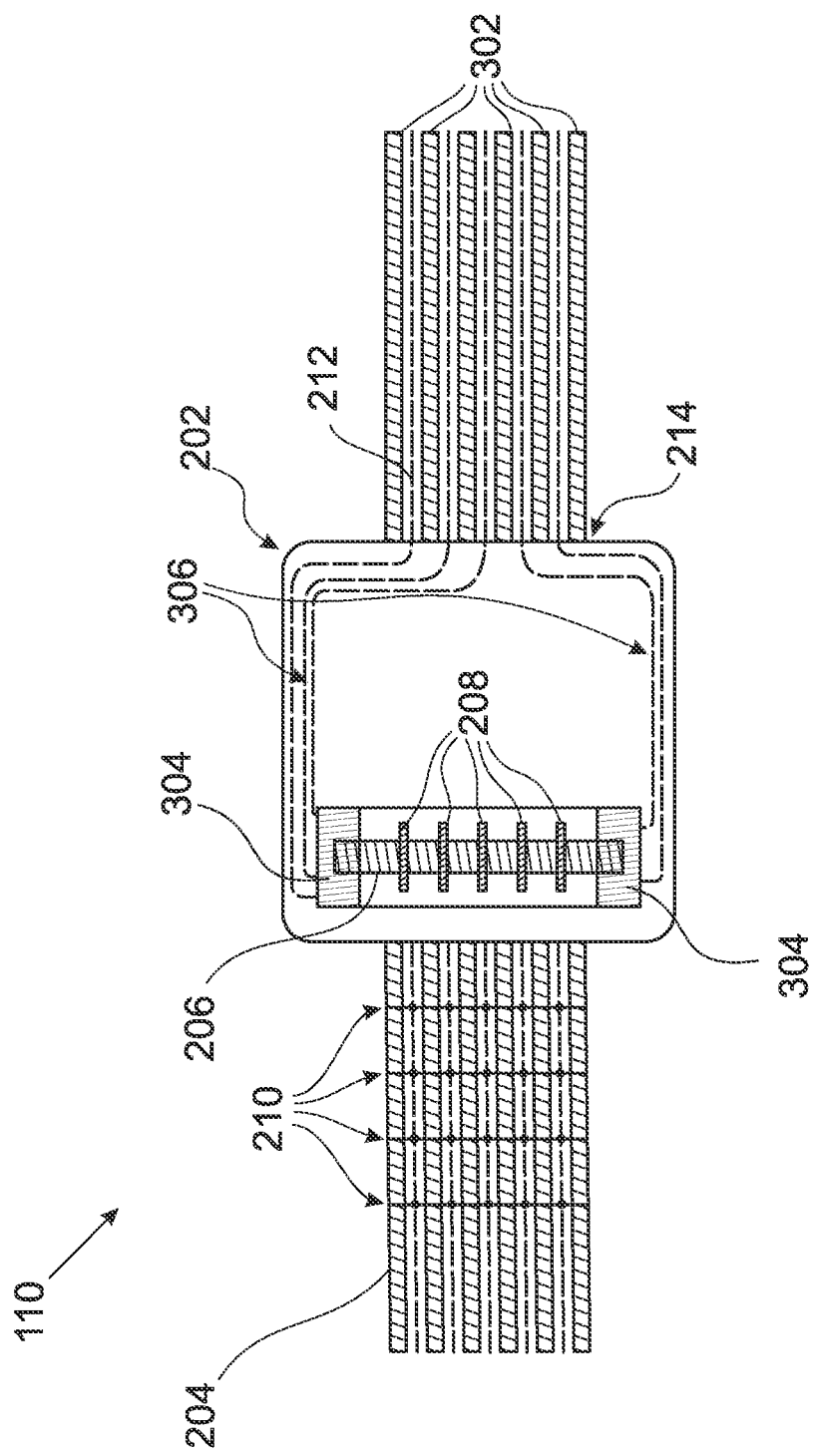
FIG. 3 depicts a top-down cross-section of a wearable device comprising a hook-based latching mechanism.

According to one or more embodiments, instructions to engage and disengage wearable device 110 cause cross-bar 206 to automatically rotate into an engaged position (as in FIG. 2A) or disengaged position (as in FIG. 2B). Specifically, FIG. 3 depicts a top-down cross-section of wearable device 110, which includes cross-bar 206, which substantially spans the width of body 202 corresponding to the width of band 204. Located on one or more terminal ends of the cross-bar 206 are motor(s) 304 that drive the rotation of the cross-bar/hook apparatus. According to various embodiments, motors 304 operate like electronic door locks. For example, electronic padlocks and related methods are described in U.S. Patent Pub. No. US20160217637A1, the contents of which are incorporated by reference as if fully set forth herein.

According to one or more embodiments, instructions to engage and disengage wearable device 110 enable a user to manually rotate cross-bar 206 into an engaged position (as in FIG. 2A) or disengaged position (as in FIG. 2B). For example, such an instruction may automatically cause a manual rotation mechanism to be engaged with the latching mechanism, or may provide access to a manual rotation mechanism within a body of the device.

As shown in FIG. 3, the hook-based latching mechanism of wearable device 110 is described herein as comprising five electrical circuits corresponding to five hook members 208 and five conductive members 212. The plurality of hook members 208 are distributed at regular intervals across cross-bar 206. Nevertheless, any number of circuit systems may be included in wearable device 110. Furthermore, more hooks and loop segments may be employed than are required for circuit systems, e.g., without a corresponding conductive member, which may provide additional stability when the latching mechanism is engaged.

In the example of FIG. 3, band 204 includes a plurality of loops 210 (e.g., wire loops) positioned at regular intervals along at least a portion of the length of the band. Loops 210 are securely fixed within each band, thereby providing positions on the band where the latching mechanism can engage the band. Any number of loops 210 may be present within band 204. As shown in FIG. 3, each of loops 210 substantially spans the width of band 204.

Figure 4A:
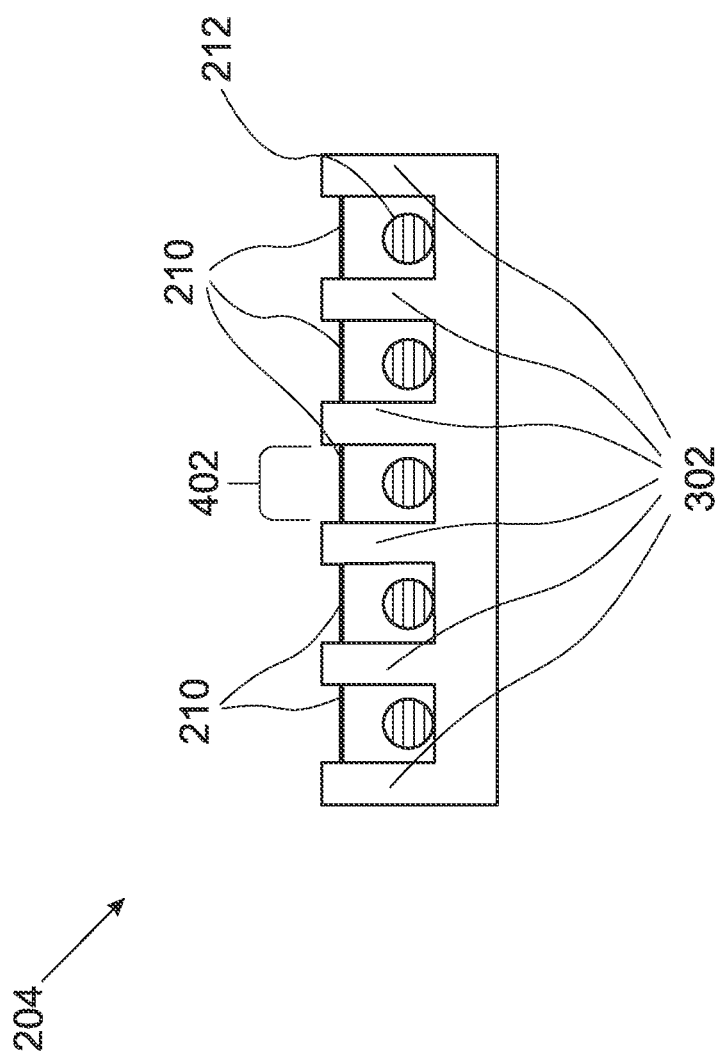
FIGS. 4A-4C depict cross-sections of a band of the wearable device comprising a hook-based latching mechanism, with and without an example hook-based latching mechanism engaged with the band.

Band 204 further comprises a plurality of channel walls 302, which define one or more channels for a plurality of conductive members 212. FIG. 4A depicts a cross-section of band 204, which shows conductive members 212 in channels (e.g., channel 402) formed by channel walls 302. Conductive members 212 are made of metal and run the length of the band. The channels may be substantially enclosed within band 204 to protect conductive members 212 from debris. FIG. 4A further depicts a loop 210 with a plurality of loop segments, where each loop segments spans a corresponding channel. The loop segments may be individual physical components, or may be part of a single physical component that substantially spans band 204. Each channel has space for a hook member 208 to fit between the loop segment affixed to the top portion of the channel and a conductive member 212 within the channel.

Figure 4B:
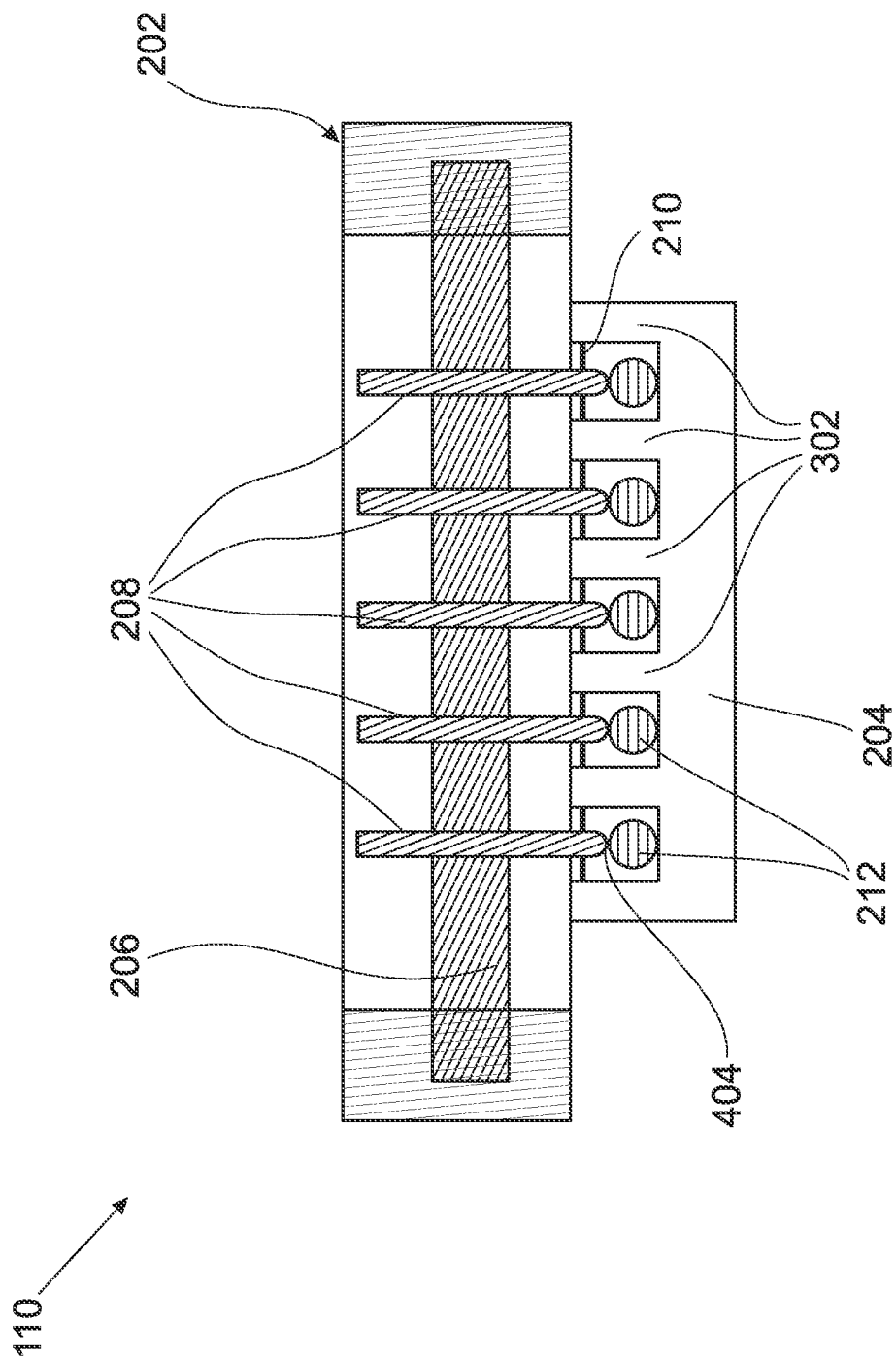

FIG. 4B depicts a cross-section of wearable device 110 that includes the cross-section of band 204 from FIG. 4A and the latching mechanism, which illustrates how hook members 208 engage with conductive members 212 when hooked on the loop segments of loop 210. When in an engaged position, hook members 208 fit between the loop segments of loop 210 and conductive members 212 to cause hook members 208 to contact corresponding conductive members 212, e.g., at contact point 404, and maintain the contact while the latching mechanism is engaged.

Returning to a discussion of FIGS. 2A-2B, FIG. 2A depicts a hook member 208 in an engaged position, where hook member 208 is rotated such that a portion of the hook member is located between a loop 210 and conductive member 212, causing the hook member to make and maintain contact with the conductive member. FIG. 2B depicts a hook member 208 in a disengaged position such that no portion of hook member 208 is located between loop 210 and conductive member 212.

Conductive members 212 are conductively connected with each corresponding hook member 208, which are also configured to conduct electricity. As shown in FIG. 3, conductive connections 306 connect conductive members 212 to the latching mechanism, which extend to each corresponding hook member 208. Conductive connections 306 may be extensions of conductive members 212, or may be additional physical components (e.g., wires). Thus, when each hook member 208 is in the engaged position, making contact with a corresponding conductive member 212 in band 204, each conductive member/hook member apparatus (or "circuit system") represents a closed electrical circuit configured to conduct an electrical current.

Figure 4C:
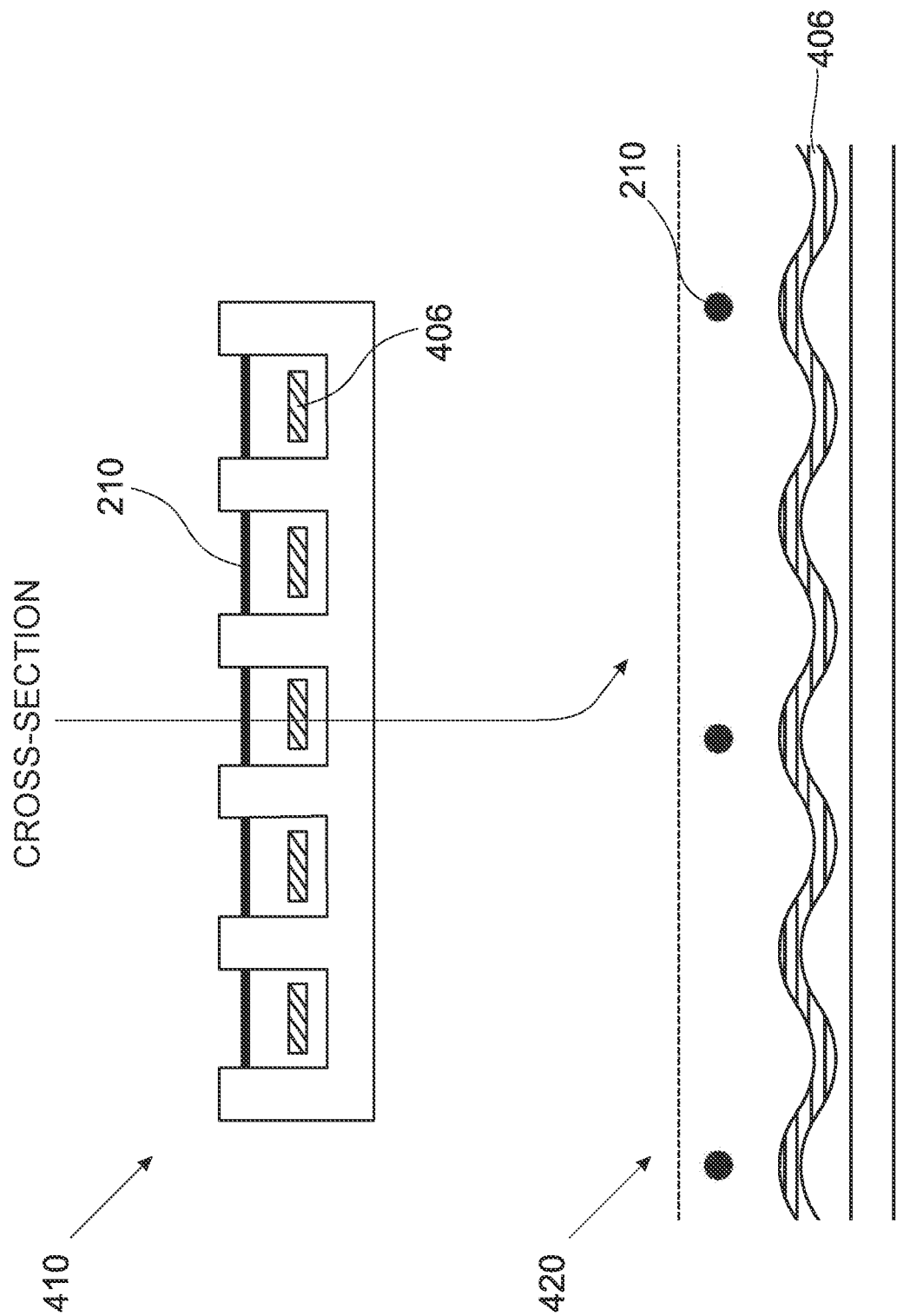

According to various embodiments, the conductive members 212 are corrugated plates, which, when the latching mechanism is disengaged, occupy at least a portion of the space within band 204 that hook members 208 occupy when engaged. FIG. 4C depicts two cross-sections 410 and 420 of band 204, which include example corrugated conductive members 406. In the non-limiting example of cross-section 410, corrugated conductive members 406 are wider than they are tall. In the non-limiting example of cross-section 420, at least some of the raised portions of corrugated conductive member 406 line up with loops 210. However, a corrugated conductive member may have any width of corrugation, including a width configured to rise independently of loops 210. Such a configuration of conductive members ensures a positive connection between hook members 208 and conductive members 212, where the connection is not rigid. In such embodiments, the conductive members deflect slightly as the hook members slide into position around the loops and make contact with the conductive members. This completes the electrical circuit of each circuit system.

3.4. Rod-Based Latching Mechanism

Figure 5:
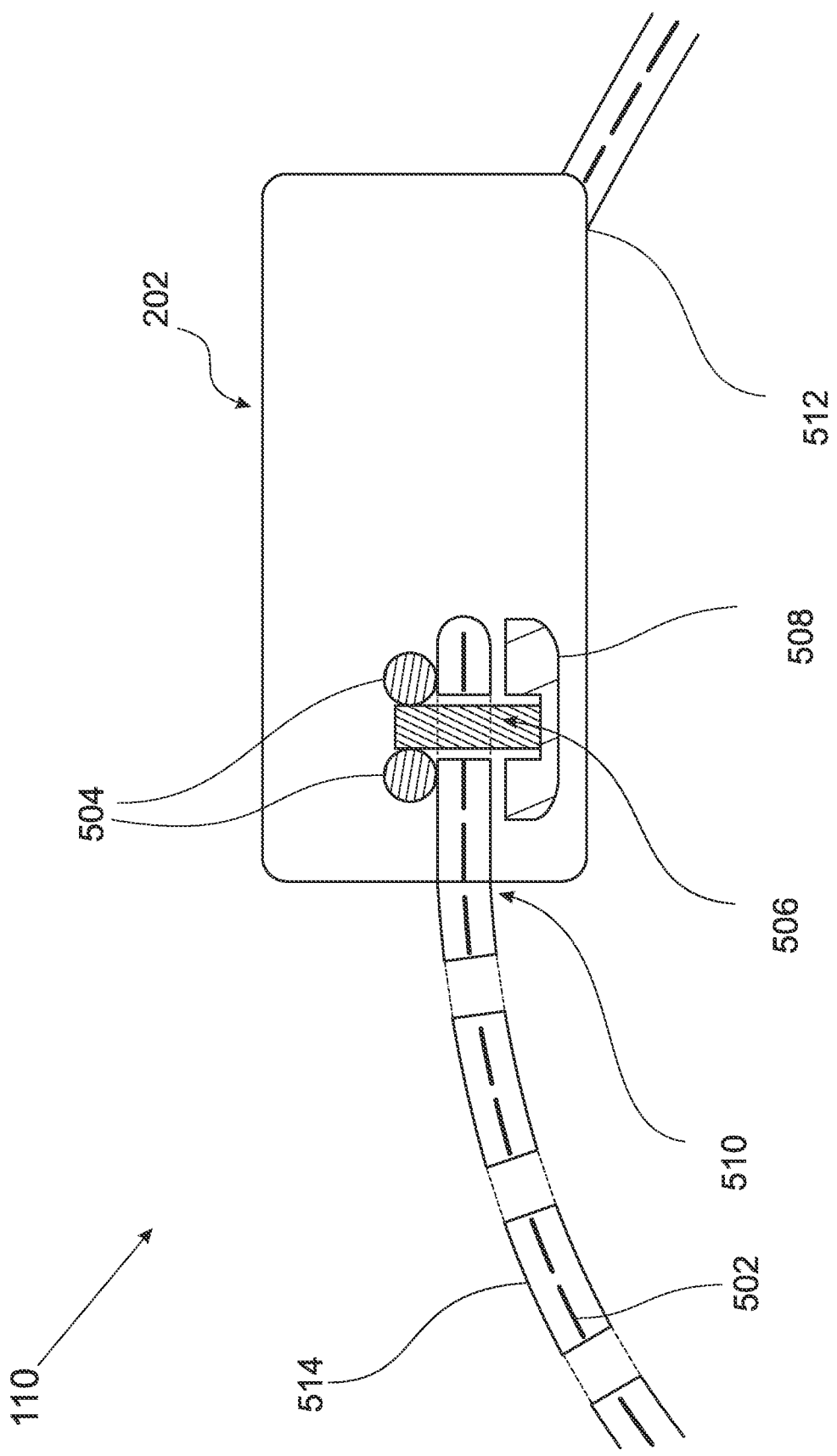
FIG. 5 depicts a cross-section of a wearable device comprising a rod-based latching mechanism that secures a body of the device to a band of the device.
Figure 6A:
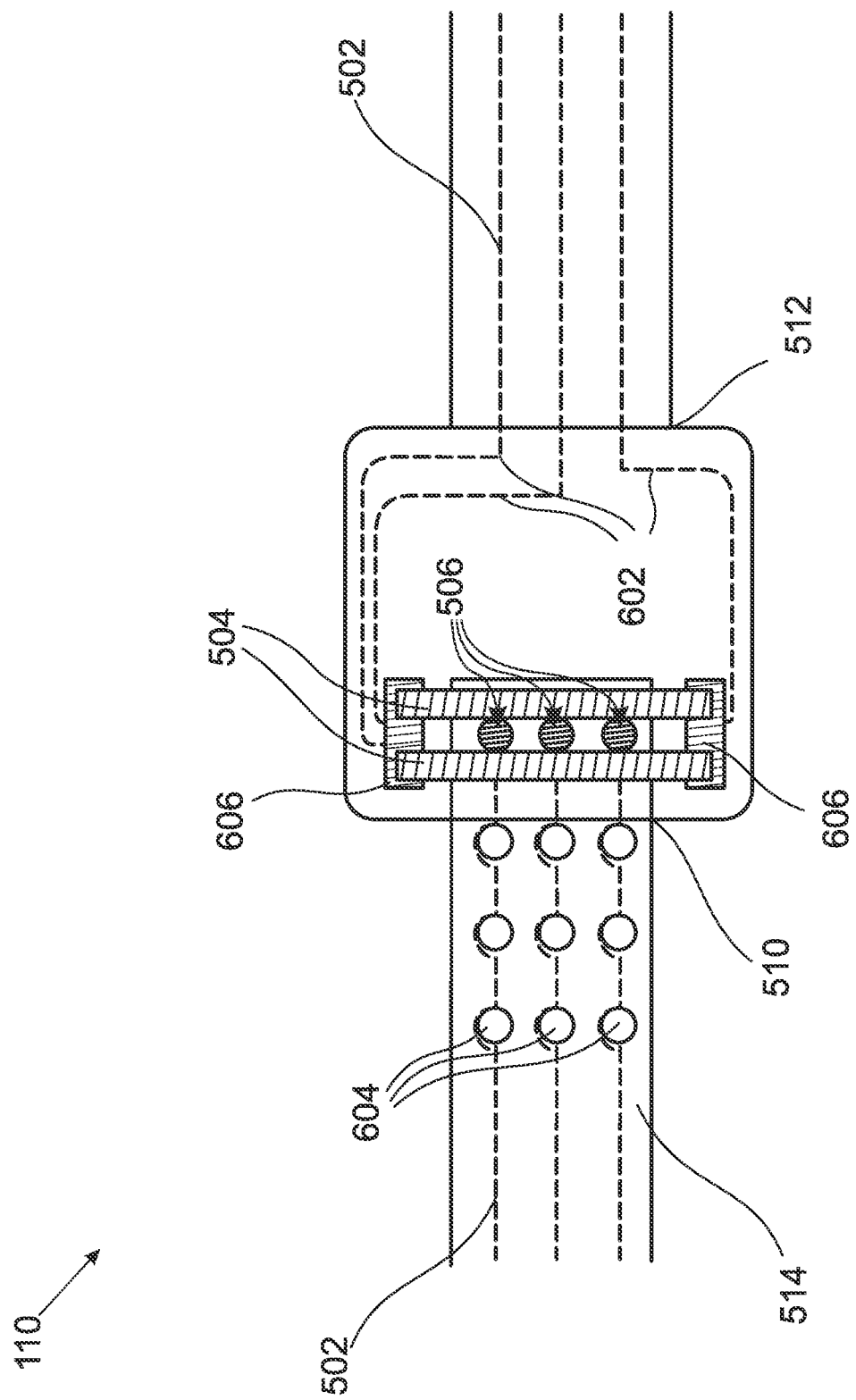
FIG. 6A-6B depict a top-down cross-section of a wearable device comprising a rod-based latching mechanism, and a cross-section of a band of the device.
Figure 9:
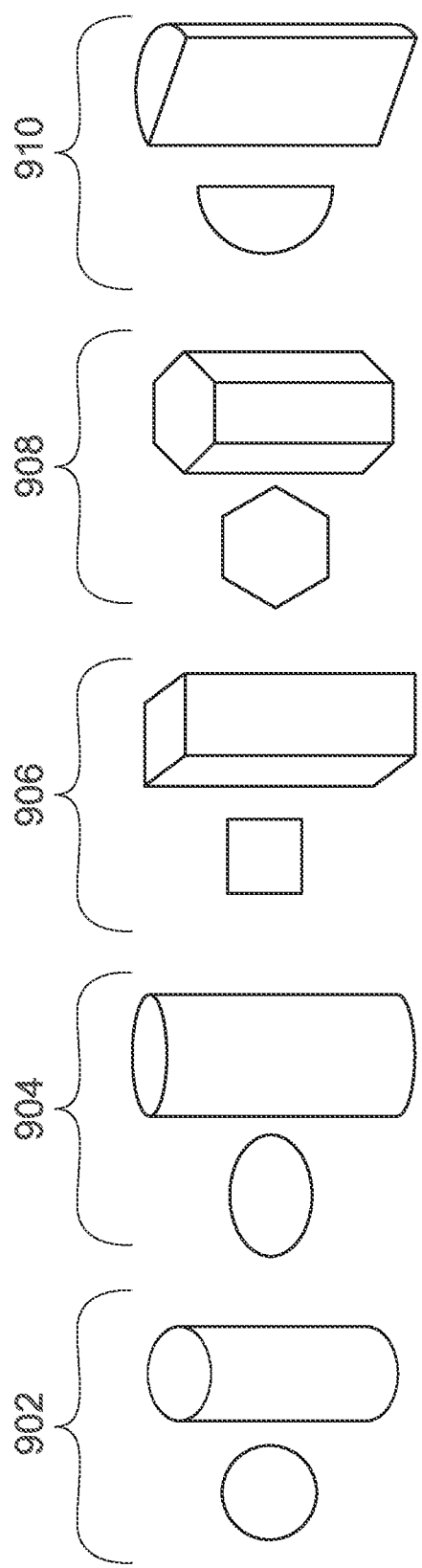
FIG. 9 depicts multiple example rod shapes.

According to various embodiments, the latching mechanism of wearable device 110 employs one or more rods that move up and down to engage and disengage the body of wearable device 110 with the band, FIG. 5 depicts a cross-section of wearable device 110 including body 202 and band 514 of the device, where one or more conductive members 502 run the length of the band. In the depicted embodiment, the latching mechanism comprises two cross-bars 504 that substantially span the width of body 202, one or more conductive rods 506, and one or more receiving plates 508. Each conductive member 502, corresponding conductive rod 506 and corresponding receiving plate 508 form a circuit system. As indicated above, wearable device 110 may include one or more circuit systems, FIG. 6A depicts three circuit systems in example wearable device 110 with three distinct rods 506 and conductive members 502. Rods 506 are depicted as cylindrical (i.e., having a circular profile); however, as depicted in FIG. 9, the rods in the rod-based latching mechanism may have any type of profile, including circular 902, 904, rectangular 906, a regular shape having any number of sides (e.g., hexagon 908), or an irregular shape having any number of sides (e.g., semicircle 910).

Each circuit system is associated with a distinct receiving plate 508, which is conductively connected to the corresponding conductive member 502 through location 512 of body 202. As shown, conductive connections 602 connect conductive members 502 to receiving plates 508, which are not shown in FIG. 6A. Conductive connections 602 may be distinct physical components from conductive members 502, or may be extensions of conductive members 502.

Figure 6B:
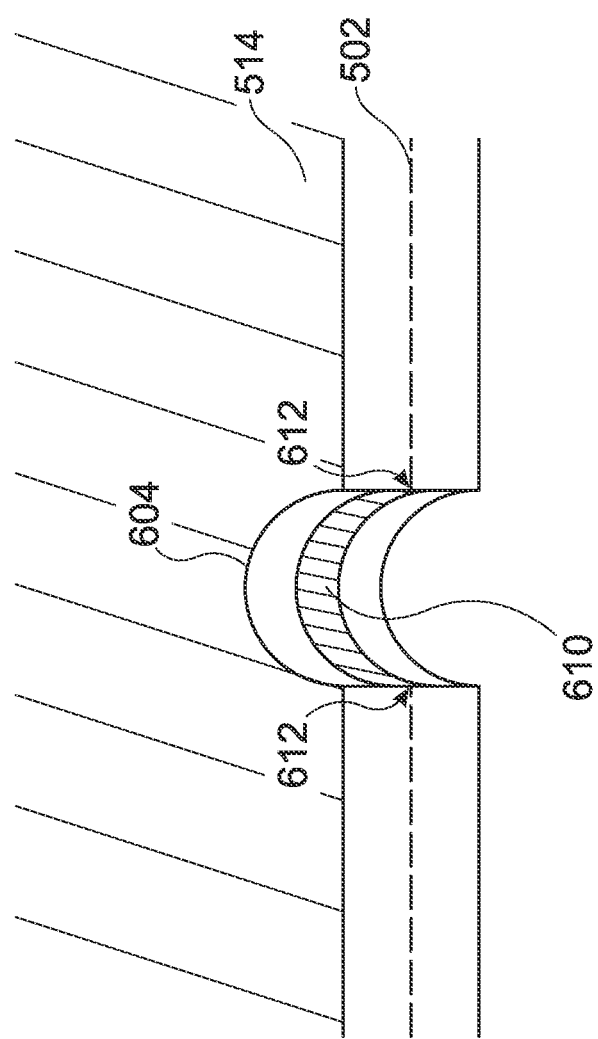

Furthermore, each conductive member 502 is exposed through corresponding holes (e.g., example set of holes 604) in band 514 such that, when engaged, corresponding rods 506 make contact with conductive members 502 through the holes. FIG. 6A depicts a conductive member 502 being exposed through a particular location within each of the holes in band 514, which is illustrative and non-limiting. Specifically, conductive members 502 may be exposed through holes in band 514 in any way, such as at two or more places within each hole. As another example, depicted by FIG. 6B, conductive member 502 may be conductively connected, within a hole 604, to a conductive plate 610, which lines at least a portion of the hole. As depicted in the example of FIG. 6B, conductive member 502 is conductively connected to conductive plate 610 at locations 612. Accordingly, plate 610 may represent a link in conductive member 502, linking two parts of conductive member 502. Furthermore, conductive member 502 may connect to plate 610 and also continue through band 514 to any further holes in the band. Because conductive members 502 are exposed through holes in band 514, when a rod 506 is resting on a corresponding receiving plate 508 through a hole in band 514, the circuit system is closed and able to conduct electricity.

As depicted in FIG. 6A, band 514 is inserted in body 502 at location 510. To engage the latching mechanism, one or more cross-bars 504 rotate (e.g., rotated by one or more motors 606 or manually rotated as described above) along the long axis. When the latching mechanism comprises two cross-bars 504, the cross-bars rotate in opposite directions (i.e., one clockwise and the other counter-clockwise) to either lift or lower the rods.

As depicted in FIGS. 8A-D, the latching mechanism may include a single cross-bar 504, where the rods are stabilized by a supporting apparatus 802 to guide the path of rod 506 as it is moved by cross-bar 504. In the example of FIGS. 8A-I), supporting apparatus 802 comprises a sleeve for each rod 506. According to various embodiments, as shown in cross-sections 800 and 810, apparatus 802 is configured to surround at least a portion of rod 506 at all times such that apparatus 802 keeps rod 506 engaged with cross-bar 504.

Figure 8A:
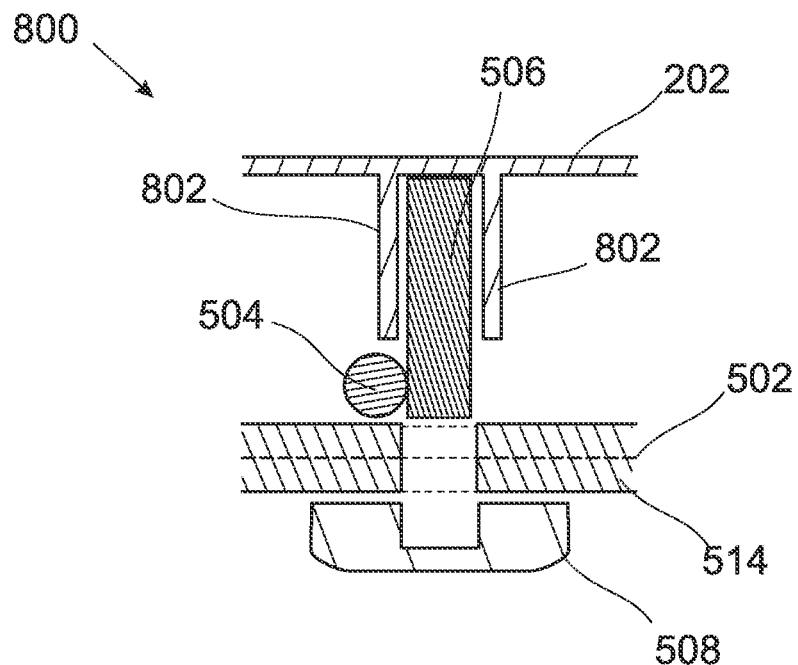
FIGS. 8A-8D depict another example implementation of a rod-based locking mechanism both engaged with and disengaged from a band of the wearable device.
Figure 8B:
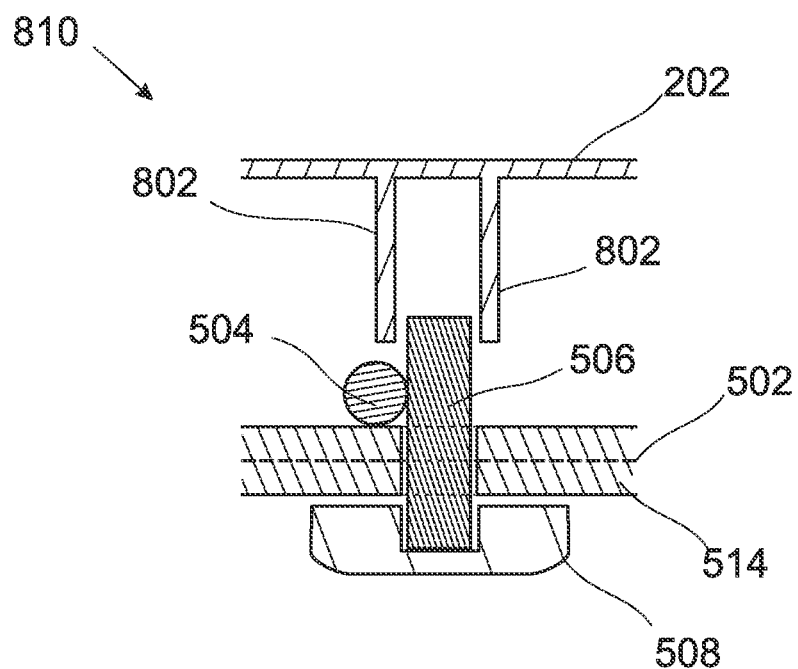
Figure 8C:
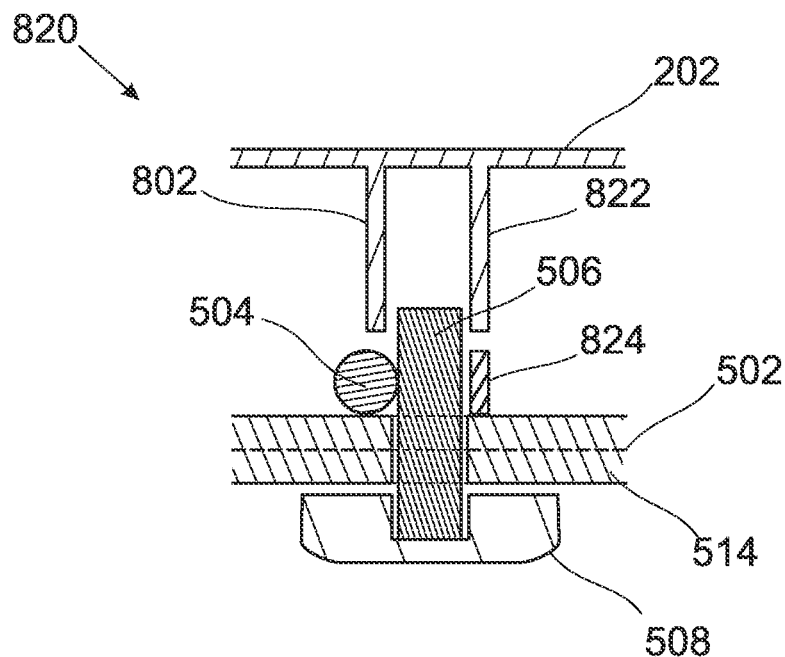
Figure 8D:
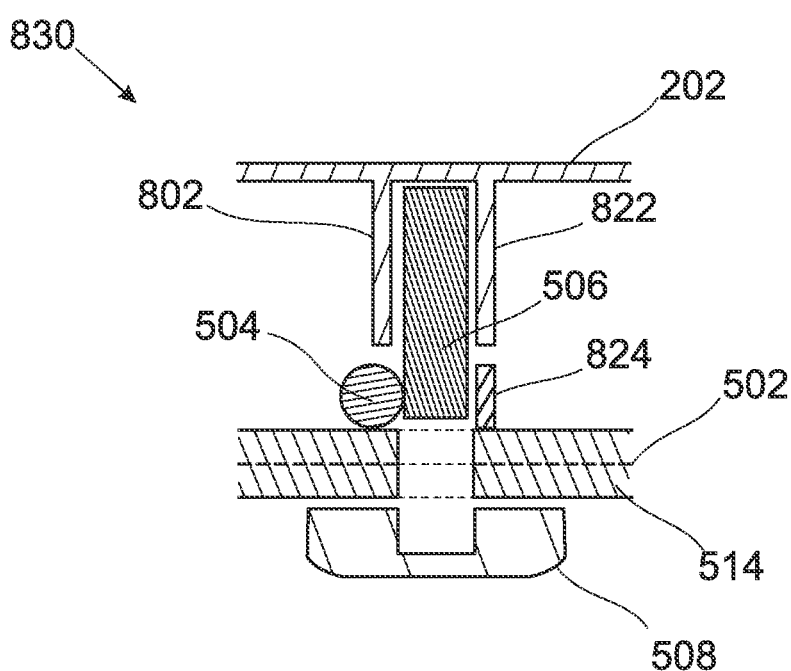

FIGS. 8C-D further depict example cross-sections 820 and 830 that include supporting apparatus 802. Cross-section 820 further includes a counter-support apparatus 822 situated across from cross-bar 504, which aides in stability of rod 506 when moving up and down as the latching mechanism disengages and engages. Supporting apparatus 802 acts as a receiving mechanism that is configured to house rod 506 when it is in the disengaged position. Counter-support apparatus 822 opposite crossbar 504 stabilizes rod 506 in the engaged and disengaged positions. Thus, there are stabilizing structures on at least two sides of rod 506 in any position of the rod (engaged, disengaged, or moving between the two). While open, counter-support apparatus 822 and structure 802 stabilize the rod. When closed, counter-support apparatus 822 and receiving plate 508 stabilize the rod. Apparatus 802 may not be configured to surround at least a portion of rod 506 at all times, e.g., when an additional support apparatus (such as counter-support apparatus 822) is used to stabilize rod 506.

Counter-support apparatus 822 may have any profile that is configured to support rod 506, which may comprise at least a portion of the profile of the rod (see, e.g., various example rod profiles in FIG. 9). Furthermore, counter-support apparatus 822 may be an extension of apparatus 802, and may or may not encase crossbar 504.

Figure 7:
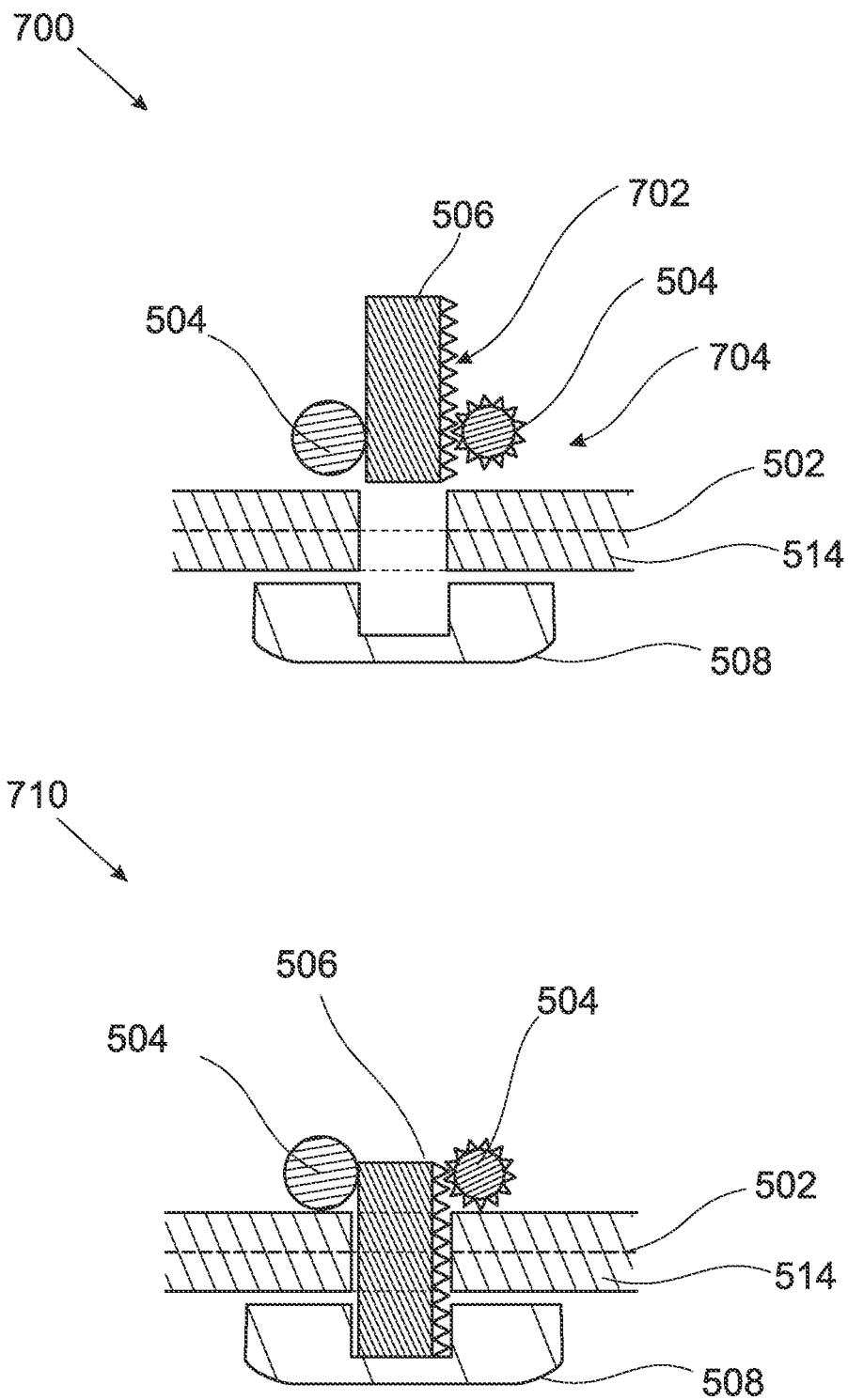
FIG. 7 depicts an example implementation of a rod-based locking mechanism both engaged with and disengaged from a band of the wearable device.

Rods 506 may engage with cross-bar 504 in any way. For example, as depicted in FIG. 7, serrations 702 on at least a portion of the vertical surface of each of rods 506 interleave with serrations 704 on at least one cross-bar 504. Serrations on rod 506 and on cross-bar 504 may have any shape that is configured to move together and interlock as cross-bar 504 rotates. Thus, cross-bar(s) 504 act as gears when rotating to move rods 506 into or out of the holes in band 514. Furthermore, as depicted in FIGS. 8A-D, cross-bar(s) 504 may engage with rods 506 using friction to move the rods. For example, the surface(s) of cross-bar(s) 504 may be configured to have a high coefficient of friction with the surfaces of rods 506. Any method of engaging rods 506 with cross-bar 504 may be used with any configuration of supporting apparatus, notwithstanding the non-limiting example configurations of wearable device 110 that are depicted in the figures.

3.5. Easy Break Points

According to various embodiments, one or more components of each of the plurality of circuit systems of wearable device 110 includes an "easy break" point designed to break (severing the electrical connection in the circuit system) when forceful removal of wearable device 110 is attempted. For example, an easy break point is configured to open the circuit system, severing the electrical connection, when over a threshold amount of pressure is placed on the physical component that includes the easy break point.

For example, a band of wearable device 110 comprises one or more "flexible" sections (e.g., a 3 cm portion of the band), which allow some amount of flex in the direction of the length of the band. To illustrate, FIG. 2A depicts a flexible section 216 in band 204, which flexes in direction 218. Inclusion of section 216 in band 204 would allow expansion during attempted removal of device 110. Section 216 may be omitted from device 110 or may be included with any kind of latching mechanism, as described in further detail below.

Flexibility of section 216 is allowed based on material used for band 204 in the section and/or material used to reinforce band 204 in that section, which allows more flex than material used in other sections of the band. According to various embodiments, less than all of a width of the band, e.g., 70% of the band width, includes the flexible material so that there is more integrity to prevent complete removal. Furthermore, one or more conductive members 212 in band 204 may be designed to be less flexible in section 216, which facilitates severing of the conductive members under attempted removal.

When an easy break point in device 110 is in the band, the band may be replaced after tampering is detected based on loss of electric current in one or more conductive members 212. For example, band attachment components are encased in body 202 of wearable device 110 such that band removal may be accomplished only after wearable device 110 is disengaged, i.e., through the authorized disengaging protocol discussed herein.

4. Wearable Caretaking Device

According to various embodiments, wearable device 110 described herein may be used as a caretaking device, where a wearer of the device is a care recipient and users of WD application 132 include one or more caretakers of the care recipient. Such a caretaking device combines technology to detect tampering and prevent unauthorized removal with caretaking functionality, such as facilitation of audio and/or video communication between the care recipient and a caretaker (e.g., one-way or two-way communication), and monitoring of various detectable conditions of a care recipient wearing the wearable device. Such detectable conditions may include one or more of a location of the care recipient, and one or more vital signs of the care recipient.

According to various embodiments, wearable device 110 stores information for detected conditions of the care recipient in database 112, such as location data, vital statistics indicating values for one or more vital signs, and also stores any communication data sent from and received by wearable device 110, etc. According to various embodiments, wearable device 110 also stores, in database 112, any emergency protocol initiation or alert dissemination performed at wearable device 110, and any alert information received at wearable device 110.

4.1. External Contact Facilitation

According to various embodiments, wearable device 110 is configured to receive communication data from and/or transmit communication data to authorized client devices 130A-N. For example, wearable device 110 may be configured to transmit and/or receive, via network 120, text data, audio data, and/or video data, to client devices 130A-N. For example, client devices 130A-N register device identifications and/or contact telephone numbers with wearable device 110 or with WD service 142 as approved contacts for wearable device 110. Furthermore, wearable device 110 and/or client devices 130A-N may be configured to transmit such communication data to WD service 142, which includes a record of the communication data in activity log 144. Furthermore, wearable device 110 may transmit communication data to local authorities registered with device, such as in connection with an emergency protocol described in further detail below. The communication data capabilities of wearable device 110 may be comparable to a standard telephonic device, or may be limited to communication with registered client devices 130A-N or registered telephone numbers.

4.2. Care Recipient Location Detection/Monitoring

According to various embodiments, wearable device 110 uses a built-in GPS sensor to identify global position data for the device. Wearable device 110 uses network 120 to periodically broadcast global position data to authorized client devices 130A-N either directly or by sending the global position data to WD service 142, which disseminates the data to authorized client devices 130A-N and stores the data in activity log 144.

According to various embodiments, global position data received at WD service 142 are saved in activity log 144 for a specified period of time. According to various embodiments, WD service 142 monitors the timing of global position data updates received from wearable device 110. If the global position data fails to be received from wearable device 110 for over a threshold amount of time while wearable device 110 is engaged on a care recipient, an alert is disseminated as described herein.

4.3. Care Recipient Vital Sign Measurement

According to various embodiments, wearable device 110 uses one or more built-in vital sign sensors to measure one or more vital signs of a wearer, such as heart rate, blood oxygen level, etc. Wearable device 110 uses network 120 to periodically broadcast vital statistics recorded for the vital signs to authorized client devices 130A-N and to WD service 142 to be stored in activity log 144, as described in detail above. WD service 142 may send the vital statistics data to authorized client devices 130A-N instead of or in addition to wearer device 110 directly sending the vital statistics data to the client devices. The vital statistics data is monitored by WD service 142 as described above for global position data. According to various embodiments, the threshold amount of time for delayed vital statistics data receipt before disseminating an alert is the same or differs from the threshold amount of time for delay in global position data receipt.

5. Caretaker Application

WD application 132, installed on client devices 130A-N allows caretakers to receive information from wearable device 110 and from WD service 142, to receive alert information, to participate in an initiated emergency protocol, and/or to initiate an emergency protocol. Using WD application 132, an authenticated user may also change the configuration of wearable device 110 and/or set up or change alert rules for wearable device 110, e.g., maintained by WE) service 142. According to various embodiments, any changes to the configuration of wearable device 110 and/or alert rules for wearable device 110 are communicated to WD service 142 and recorded in activity log 144.

According to various embodiments, WD application 132 provides, to client devices 130A-N, real-time updates of location data and/or vital statistics data for a wearer of wearable device 110. WD application 132 requires a user to successfully authenticate themselves at client devices 130A-N prior to accessing information from wearable device 110 to protect the sensitive information being provided by wearable device 110. Users may have varying levels of privileges, such as primary users having all privileges, and secondary users who have restricted privileges regarding one or more of zone definition, alert rule definition, access to alerts, emergency protocol initiation, engagement, disengagement, access to data updates from wearer device 110, etc. According to various embodiments, WD service 142 maintains information regarding the privileges of various users, and enforces privilege restrictions. In such embodiments, wearer device 110 communicates with one or more of client devices 130A-N via WD service 142.

5.1. Location Display

According to various embodiments, WD application 132 causes global location data received from wearable device 110 to be displayed in a graphical user interface (GUI) on a display apparatus for a client device 130. Global location data may be displayed in any way.

Figure 10A:
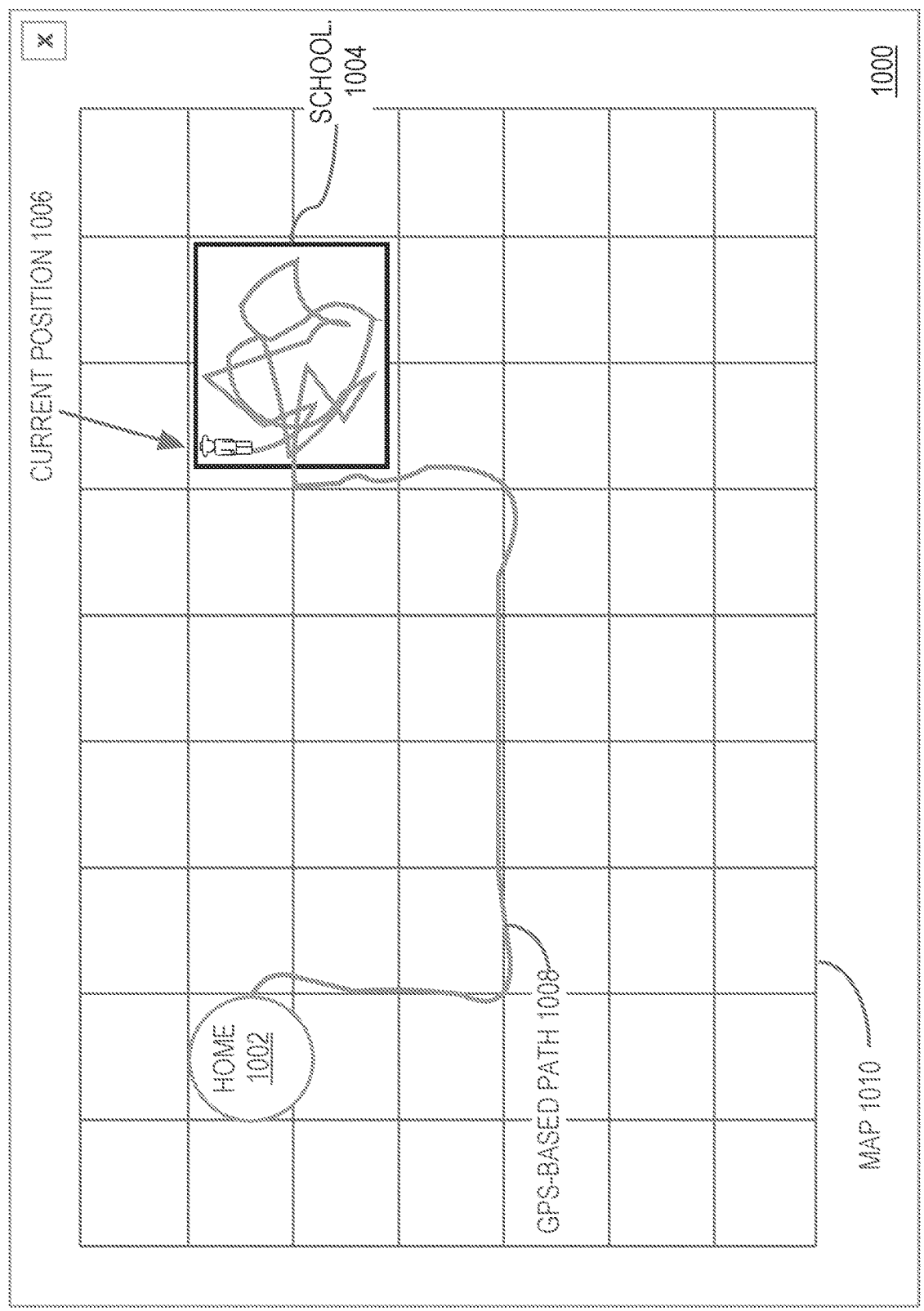
FIGS. 10A-10B depict example graphical user interfaces for a caretaker application running at a client device.
Figure 10B:
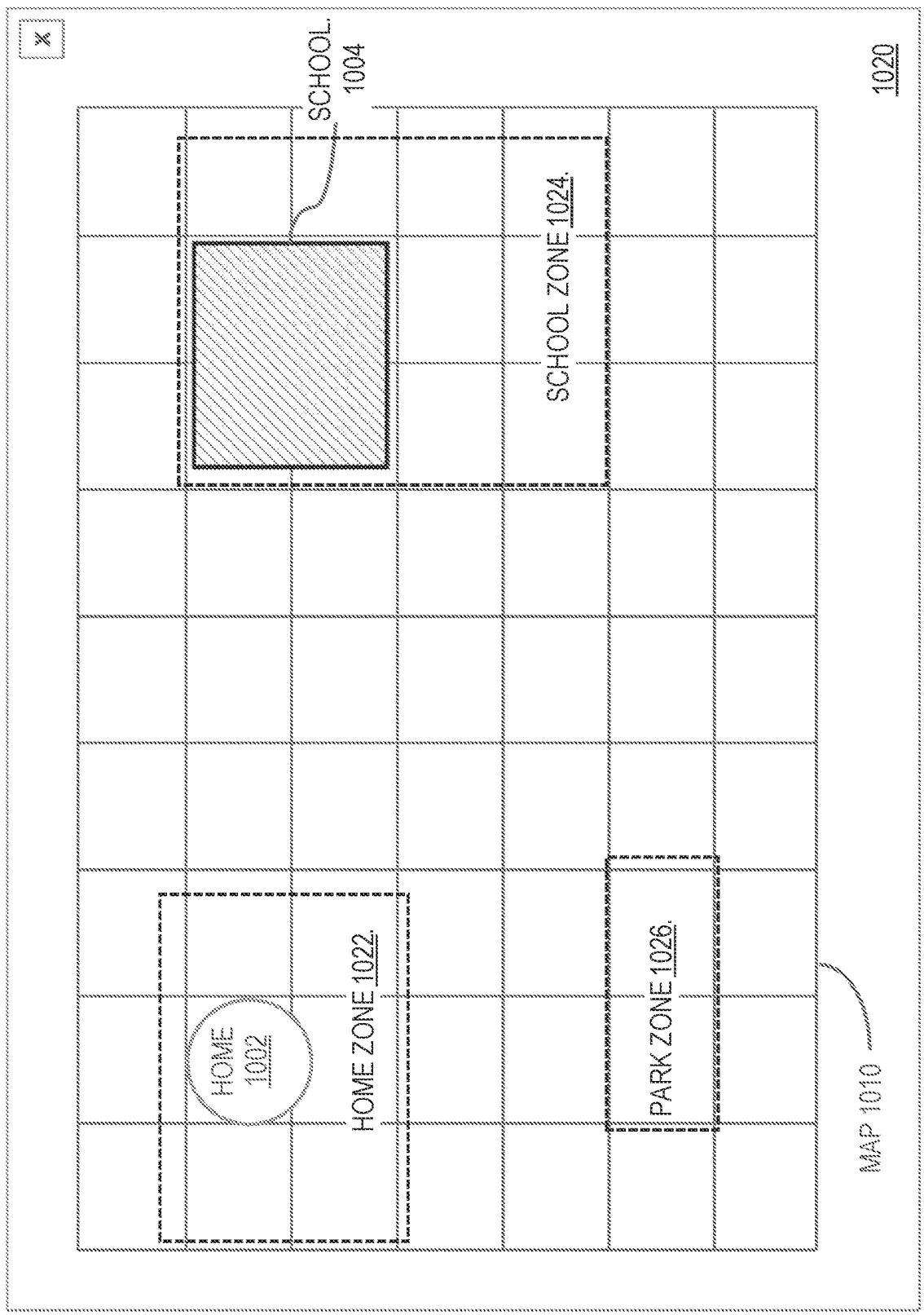

FIGS. 10A-10B depict example GUIs 1000 and 1020 for WD application 132. Specifically, example GUI 1000 of FIG. 10A depicts a map 1010 with identified locations, e.g., home 1002 and school 1004. These locations may be automatically identified based on publicly-available map information, or may be user-defined via information supplied by an authenticated user through WD application 132. Example GUI 1000 displays, in map 1010, a current position 1006 of a care recipient wearing wearable device 110, the location of which on map 1010 is based on the most recent global position data received from wearable device 110. WD application 132 may receive global position information directly from wearable device 110 or from WD service 142, via network 120. Example GUI 1000 further displays, in map 1010, a path 1008 that is based on historical global position data from wearable device 110. According to various embodiments, a user may mouse-over one or more aspects of GUI 1000 to view additional metadata, such as timestamps, associated with the global position data on which the aspect of the GUI is based.

5.2. Zone-Based Location Alert Rules

According to one or more embodiments, WD service 142 maintains an alert rule set 146 that defines one or more rules based on which alerts may be disseminated, as described in further detail below. One or more of the rules in rule set 146 may be location-based. Specifically, one or more rules be associated with a geographic location (referred to herein as a "zone") and, potentially, with one or more time ranges. Location-based rules allow users to specify when a location-based alert should be disseminated, e.g., if the global location data from wearer device 110 deviates from an identified zone during an associated time range for over a threshold amount of time. The threshold amount of time may be a default amount of time, or may be identified for particular rules.

WD application 132 allows authenticated users (e.g., with permission to define zones) to define one or more zones for wearable device 110. Such zone definitions are maintained by WD service 142. FIG. 10B depicts an example GUI 1020 that includes map 1010 through which a user may define one or more geographic zones. GUI 1020 includes example zones 1022-1026, which are defined by authenticated users registered for wearable device 110.

FIG. 11 depicts an example alert rule set 146 generated by one or more registered users and maintained by WD service 142. Specifically, alert rule set 146 comprises example rules 1102-1118, which comprise definition/metadata information 1120-1128. The rules in FIG. 11 are illustrative, and alert rules for wearable device 110 may comprise any kind of definition information or metadata information, which may include one or more of the depicted types of definition/metadata information and/or may include other types of definition/metadata information.

Each of rules 1102-1108 and 1114-1118 include location information 1120, which may identify a location basis for a rule in any way. For example, rules 1102-1108 and 1118 identify zones defined via WD application 132, e.g., using GUI 1020. (Note that zone 1028 identified in rule 1118 is not depicted in FIG. 10, e.g., because the location of zone 1028 is outside the boundaries of the depicted map 1010.) Rules 1110-1112 identify a "no alert" location, which is a NULL location indicating that no location-based rule is to be applied during the indicated time ranges. Further, rules 1114-1116 identify a relative location defined by a location of a device of a particular user and a distance, and as such incorporate dynamic zone definitions for the rules that move with the identified users.

Days information 1122 and times information 1124 define the time ranges during which each rule is applicable. Days information 1122 may identify days in any way, including repeated days (such as "M-F" meaning Monday through Friday of every week as in rule 1102, or "first weekend of every month" as in rule 1116), "ALL" meaning that the rule is always applicable, particular dates as in rule 1110, etc. Exceptions information 1126 identify any days during which the indicated rule (e.g., with a repeating time range) is not applicable.

Group information 1128 allows users to logically group rules together. For example, rules 1102, 1104, and 1112 belong to the group "school day", and rules 1110, 1116, and 1118 belong to the group "father". Rules may be prioritized individually or based on group membership to determine which rule is applied in the case that multiple conflicting rules are applicable at a given time.

6. Alert Dissemination

According to various embodiments, when an alert is disseminated, alert information is automatically sent to one or more of client devices 130A-N either directly from wearable device 110 or through WD service 142, which also receives the alert information. WD service 142 stores the alert information in activity log 144. Furthermore, alert information may also be sent to one or more support units, such as a security service, law enforcement, a support team for wearable devices, etc. For example, an alert that is disseminated based on initiation of the emergency protocol is automatically sent to local authorities including law enforcement.

According to embodiments, alert information is prominently displayed in WD application 132, and may also cause an alert sound and/or an alert display to be displayed over a current display by a client device 130, whether or not the current display is controlled by WD application 132. According to embodiments alert information includes one or more of: a type of event that caused alert dissemination, a timestamp for the event, global location information for the wearable device, any communication data sent by wearable device 110 within a threshold amount of time from the event, etc.

7. Emergency Protocol

An emergency protocol may be automatically or manually triggered, which causes one or more emergency-response actions to be performed. Emergency indicators include one or more of: unauthorized removal of the wearable device from the wearer, the loss of electric current in the one or more circuit systems of the wearable device, cessation of detection of one or more vital signs at the wearable device, activation of emergency protocol from a client device, or manual activation of emergency protocol at the wearable device. Manual activation of emergency protocol at wearable device 110 may be performed in any way, such as based on activation of one or more physical or logical controls on the device.

For example, after wearable device 110 is engaged, wearable device 110 and/or WD service 142 are able to detect emergency indicators, which trigger initiation of the emergency protocol. For example, if all circuit systems of wearable device 110 are broken without wearable device 110 being disengaged by an authorized user as described herein, this indicates that the band was severed or wearable device 110 was broken off of the care recipient, and wearable device 110 and/or WD service 142 automatically initiates emergency protocol. Similarly, detecting that one or more of the circuit systems within wearable device 110 are broken may result in initiation of an emergency protocol.

According to various embodiments, initiation of the emergency protocol causes wearable device 110 to activate one or both of video and audio transmission, which is automatically transmitted to WD service 140 and/or to client devices 130A-N (via WD application 132 or other communication mechanism) and/or to a support service. The video and audio may be live or real-time, or may be recorded during a timeframe that relates to the time that the emergency protocol was initiated, e.g., during a time period previous to and/or after the emergency protocol was initiated. As another example, initiation of the emergency protocol causes an alert to be disseminated. As another example, initiation of the emergency protocol causes wearable device 110 to provide location information detected at the time of the protocol initiation (or the last location detected prior to protocol initiation) to client devices 130A-N, and/or to WD service 142, and/or to other emergency contacts such as a wearable device support service or law enforcement. According to various embodiments, the location information detected in connection with initiation of emergency protocol is saved, e.g., at activity log 144. Audio and/or video data from the emergency activation may also be saved at computer-readable media in wearable device, e.g., as a back-up for failed transmission.

According to various embodiments, the emergency protocol can be activated from WD application 132, e.g., by activation of a graphical user interface control. Such manual activation of emergency protocol may be useful when, for instance, a caretaker notices concerning vital statistics, or the care recipient transmits concerning audio/video, or the care recipient does not respond through wearable device 110. Furthermore, according to various embodiments, the caretaker can notify law enforcement directly from WD application 132. Further, caretakers can choose to notify law enforcement, e.g., through an option on WD application 132, if any alerts or alarms are determined to justify it. This includes prolonged loss of wearable device signal (such as a heartbeat message from wearable device 110), a problem with the vital statistics monitoring, an unexpected change in location, concerning audio or video transmission from wearable device 110, etc.

8. Alternatives and Extensions

The activity on wearable device 110 can also be monitored by a support team that serves to monitor alerts and alarms. According to various embodiments, this support team does not have access to the care recipient's wearable device, but receives alerts and alarms when problems occur. The support team may then contact caretakers and/or law enforcement depending on the circumstance and/or trigger an emergency protocol for wearable device 110. Circumstances that warrant notification of caretakers and/or law enforcement and/or triggering of the emergency protocol may include cessation in transmission from wearable device 110, health vital alerts, unauthorized removal of or tampering with wearable device 110, emergency activation of wearable device 110, an unexpected change in wearable device location, etc.

9. Hardware Overview

An application, such as WD application 132 or WD service 142, runs on a computing device and comprises a combination of software and allocation of resources from the computing device. Specifically, an application is a combination of integrated software components and an allocation of computational resources, such as memory, and/or processes on the computing device for executing the integrated software components on a processor, the combination of the software and computational resources being dedicated to performing the stated functions of the application.

One or more of the functions attributed to any process described herein, may be performed any other logical entity that may or may not be depicted in FIG. 1, according to one or more embodiments. In some embodiments, each of the techniques and/or functionality described herein is performed automatically and may be implemented using one or more computer programs, other software elements, and/or digital logic in any of a general-purpose computer or a special-purpose computer, while performing data retrieval, transformation, and storage operations that involve interacting with and transforming the physical state of memory of the computer.

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 12:
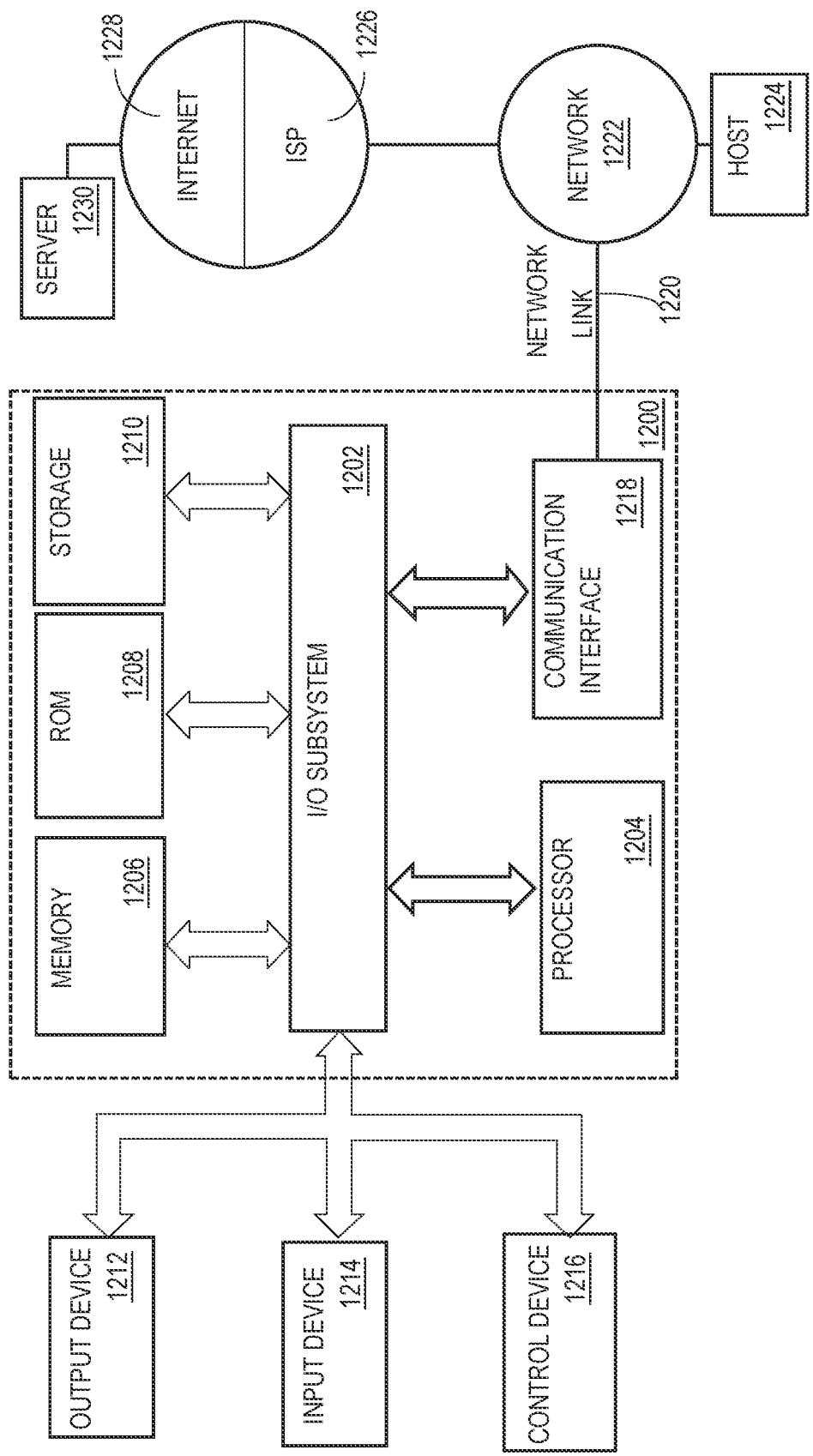
FIG. 12 is a block diagram that illustrates a computer system upon which various embodiments of the invention may be implemented.

For example, FIG. 12 is a block diagram that illustrates a computer system 1200 upon which various embodiments of the invention may be implemented. Computer system 1200 includes a bus 1202 or other communication mechanism for communicating information, and a hardware processor 1204 coupled with bus 1202 for processing information. Hardware processor 1204 may be, for example, a general-purpose microprocessor.

Computer system 1200 also includes a main memory 1206, such as a random access memory (RAM) or other dynamic storage device, coupled to bus 1202 for storing information and instructions to be executed by processor 1204. Main memory 1206 also may be used for storing temporary variables or other intermediate information during execution of instructions to be executed by processor 1204. Such instructions, when stored in non-transitory storage media accessible to processor 1204, render computer system 1200 into a special-purpose machine that is customized to perform the operations specified in the instructions.

Computer system 1200 further includes a read only memory (ROM) 1208 or other static storage device coupled to bus 1202 for storing static information and instructions for processor 1204. A storage device 1210, such as a magnetic disk, optical disk, or solid-state drive is provided and coupled to bus 1202 for storing information and instructions.

Computer system 1200 may be coupled via bus 1202 to a display 1212, such as a cathode ray tube (CRT), for displaying information to a computer user. An input device 1214, including alphanumeric and other keys, is coupled to bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

Computer system 1200 may implement the techniques described herein using customized hard-wired logic, one or more ASICs or FPGAs, firmware and/or program logic which in combination with the computer system causes or programs computer system 1200 to be a special-purpose machine. According to one embodiment, the techniques herein are performed by computer system 1200 in response to processor 1204 executing one or more sequences of one or more instructions contained in main memory 1206. Such instructions may be read into main memory 1206 from another storage medium, such as storage device 1210. Execution of the sequences of instructions contained in main memory 1206 causes processor 1204 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 1210. Volatile media includes dynamic memory, such as main memory 1206. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1202. Transmission media can also take the form of acoustic or light waves, such as those generated during radio-wave and infra-red data communications.

Various forms of media may be involved in carrying one or more sequences of one or more instructions to processor 1204 for execution. For example, the instructions may initially be carried on a magnetic disk or solid-state drive of a remote computer. The remote computer can load the instructions into its dynamic memory and send the instructions over a telephone line using a modem. A modem local to computer system 1200 can receive the data on the telephone line and use an infra-red transmitter to convert the data to an infra-red signal. An infra-red detector can receive the data carried in the infra-red signal and appropriate circuitry can place the data on bus 1202. Bus 1202 carries the data to main memory 1206, from which processor 1204 retrieves and executes the instructions. The instructions received by main memory 1206 may optionally be stored on storage device 1210 either before or after execution by processor 1204.

Computer system 1200 also includes a communication interface 1218 coupled to bus 1202. Communication interface 1218 provides a two-way data communication coupling to a network link 1220 that is connected to a local network 1222. For example, communication interface 1218 may be an integrated services digital network (ISDN) card, cable modem, satellite modem, or a modem to provide a data communication connection to a corresponding type of telephone line. As another example, communication interface 1218 may be a local area network (LAN) card to provide a data communication connection to a compatible LAN. Wireless links may also be implemented. In any such implementation, communication interface 1218 sends and receives electrical, electromagnetic, or optical signals that carry digital data streams representing various types of information.

Network link 1220 typically provides data communication through one or more networks to other data devices. For example, network link 1220 may provide a connection through local network 1222 to a host computer 1224 or to data equipment operated by an Internet Service Provider (ISP) 1226. ISP 1226 in turn provides data communication services through the worldwide packet data communication network now commonly referred to as the "Internet" 1228. Local network 1222 and Internet 1228 both use electrical, electromagnetic, or optical signals that carry digital data streams. The signals through the various networks and the signals on network link 1220 and through communication interface 1218, which carry the digital data to and from computer system 1200, are example forms of transmission media.

Computer system 1200 can send messages and receive data, including program code, through the network(s), network link 1220 and communication interface 1218. In the Internet example, a server 1230 might transmit a requested code for an application program through Internet 1228, ISP 1226, local network 1222 and communication interface 1218.

The received code may be executed by processor 1204 as it is received, and/or stored in storage device 1210, or other non-volatile storage for later execution.

What is claimed is:

1. A wearable device comprising:
   a body comprising a latching mechanism, one or more processors, and a communication interface; and
   a band affixed to the body, a length of the band being configured to encircle a wearer's limb, the band and the body comprising a plurality of circuit systems, each circuit system of the plurality of circuit systems being configured to conduct an electric current when the latching mechanism is engaged with the band, wherein the latching mechanism comprises one of a set of rods or a set of hook members, wherein one of one of said set of rods or said set of hook members are electrically integrated into each circuit system of the plurality of circuit systems;
   the one or more processors being configured to:
   while the latching mechanism is engaged with the band, detect loss of electric current in one or more circuit systems comprising less than all of the plurality of circuit systems,
   responsive to detecting the loss of electric current in the one or more circuit systems, transmit information regarding the loss of electric current in the one or more circuit systems to a destination application.

2. The wearable device of claim 1, wherein:
   the information regarding the loss of electric current in the one or more circuit systems comprises one or more identifiers of the one or more circuit systems;
   the destination application is a service that maintains a plurality of ignore flags for the plurality of circuit systems;
   responsive to determining that a particular ignore flag for a particular circuit system, of the one or more circuit systems, is not set, the service causes alert information, based on the information regarding the loss of electric current in the one or more circuit systems, to be disseminated to one or more client devices associated with the wearable device.

3. The wearable device of claim 1, wherein:
   the body further comprises one or more sensors configured to detect one or more attributes of the wearer comprising one or more of: location, heart rate, blood oxygen level, or step count; and
   the one or more processors are further configured to transmit the one or more attributes of the wearer detected by the one or more sensors, via the communication interface, to a destination application.

4. The wearable device of claim 3, wherein:
   the body further comprises one or more computer-readable media; and
   the one or more processors are further configured to store the one or more attributes of the wearer, detected by the one or more sensors, at the one or more computer-readable media.

5. The wearable device of claim 1, wherein the one or more processors are further configured to:
   receive an instruction to engage or disengage the wearable device;
   responsive to the instruction being from an authorized source, causing the latching mechanism to engage or disengage according to the instruction.

6. The wearable device of claim 5, wherein the one or more processors are further configured to determine whether the instruction is from an authorized source by:
   determining that a client device that issued the instruction is physically communicatively connected to the wearable device; and
   determining that a user that is authorized to issue the instruction has authenticated with a client application on the client device;
   wherein determining that the instruction is from an authorized source is based on the client device being physically communicatively connected to the wearable device and the authorized user being authenticated with the client application on the client device.

7. The wearable device of claim 1, wherein the one or more processors are further configured to:
   detect one or more emergency indicators comprising one or more of:
   unauthorized removal of the wearable device from the wearer, the loss of electric current in the one or more circuit systems, cessation of detection of one or more vital signs at the wearable device, activation of emergency protocol from a client device, or manual activation of emergency protocol at the wearable device; and
   responsive to detecting the one or more emergency indicators, perform one or more emergency-response actions comprising one or more of:
   transmitting data recorded in connection with detecting the one or more emergency indicators to a destination application,
   storing data recorded in connection with detecting the one or more emergency indicators in computer-readable media comprised in the body,
   transmitting data recorded previous to detecting the one or more emergency indicators to a destination application,
   initiation of audio and/or video recording at the wearable device, or
   transmitting audio and/or video recording data to a destination application and/or to law enforcement.

8. The wearable device of claim 1, wherein one or more physical components of each circuit system, of the plurality of circuit systems, is configured to open said each circuit system when over a threshold amount of pressure is placed on the one or more physical components.

9. The wearable device of claim 1, wherein one or both of the body and the band are reinforced with steel.

10. A wearable device comprising:
    a body comprising a hook-based latching mechanism, one or more processors, and a communication interface; and
    the hook-based latching mechanism comprising:
    a rotatable cross-bar, and
    a set of hook members rigidly connected to the rotatable cross-bar;
    a band affixed to the body, a length of the band being configured to encircle a wearer's limb, the band comprising:
    a set of conductive members positioned within the band and running the length of the band, a first end of each conductive member, of the set of conductive members, being conductively connected to a corresponding hook member of the set of hook members, and
    one or more loop members substantially spanning a width of the band, each loop member of the one or more loop members being disposed adjacent to the set of conductive members within the band;

the hook-based latching mechanism being configured to engage with the band by:
  rotating the rotatable cross-bar, said rotating causing each hook member of the set of hook members to:
  (a) slide under a particular loop member, of the one or more loop members, and
  (b) make and maintain contact with a corresponding conductive member of the set of conductive members;
each hook member, of the set of hook members, and each corresponding conductive member, of the set of conductive members, forming a respective circuit system, of a set of circuit systems, configured to conduct an electric current when the hook-based latching mechanism is engaged with the band;
the one or more processors being configured to:
  while the hook-based latching mechanism is engaged with the band, detect loss of electric current in one or more circuit systems of the set of circuit systems, and
  responsive to detecting loss of electric current in the one or more circuit systems, transmit information regarding the loss of electric current in the one or more circuit systems, via the communication interface, to a destination application.

11. The wearable device of claim 10, wherein:
the body further comprises one or more sensors configured to detect one or more attributes of the wearer comprising one or more of: location, heart rate, blood oxygen level, or step count; and
the one or more processors are further configured to transmit the one or more attributes of the wearer detected by the one or more sensors, via the communication interface, to a destination application.

12. The wearable device of claim 10, wherein the hook-based latching mechanism further comprises one or more motors that are configured to rotate the rotatable cross-bar.

13. The wearable device of claim 10, wherein one or more physical components of each circuit system, of the set of circuit systems, is configured to break when over a threshold amount of pressure is placed on the one or more physical components.

14. A wearable device comprising:
a three-dimensional body having three mutually perpendicular axes along a width, a height, and a length, the body comprising a rod-based latching mechanism, one or more processors, and a communication interface;
the rod-based latching mechanism comprising:
  a rotatable cross-bar, a length of which substantially spans a first axis of the three axes of the body,
  a set of rods each having a length longer than a width and a height, the length of each rod running being disposed along a second axis of the three axes of the body, each rod being configured to be moved by the rotatable cross-bar, and
  a set of conductive receiving plates, each of which is configured to touch a corresponding rod, of the set of rods, when the rod-based latching mechanism is engaged;
a band affixed to an end of a third axis of the three axes of the body, a length of the band being configured to encircle a wearer's limb, the band comprising:
  one or more sets of holes, each set of holes being configured to receive the set of rods,
  a set of conductive members positioned within the band and running the length of the band, a first end of each conductive member, of the set of conductive members, being conductively connected to a corresponding conductive receiving plate of the set of conductive receiving plates, and
  wherein for each conductive member, of the set of conductive members, a corresponding hole of each of the one or more sets of holes exposes said each conductive member;
the rod-based latching mechanism being configured to engage with the band by:
  rotating the rotatable cross-bar, said rotating causing each rod, of the set of rods, to:
  (a) enter a corresponding hole, of a particular set of holes of the one or more sets of holes,
  (b) make and maintain contact with a corresponding conductive member exposed through the corresponding hole, and
  (c) make and maintain contact with a corresponding conductive receiving plate of the set of conductive receiving plates;
each rod, of the set of rods, each corresponding conductive member, of the set of conductive members, and each corresponding conductive receiving plate of the set of conductive receiving plates forming a respective circuit system, of a set of circuit systems, configured to conduct an electric current when the rod-based latching mechanism is engaged with the band;
the one or more processors being configured to:
  while the rod-based latching mechanism is engaged with the band, detect loss of electric current in one or more circuit systems of the set of circuit systems, and
  responsive to detecting loss of electric current in the one or more circuit systems, transmit information regarding the loss of electric current in the one or more circuit systems, via the communication interface, to a destination application.

15. The wearable device of claim 14, wherein:
the body further comprises one or more sensors configured to detect one or more attributes of the wearer comprising one or more of: location, heart rate, blood oxygen level, or step count; and
the one or more processors are further configured to transmit the one or more attributes of the wearer detected by the one or more sensors, via the communication interface, to a destination application.

16. The wearable device of claim 14, wherein the rod-based latching mechanism further comprises one or more motors that are configured to rotate the rotatable cross-bar.

17. The wearable device of claim 14, wherein:
the rotatable cross-bar has a set of cross-bar ridges substantially spanning the length of the rotatable cross-bar;
each rod, of the set of rods, has a set of rod ridges; and
each rod is configured to be moved by the rotatable cross-bar based on the set of rod ridges of said each rod interleaving with the set of cross-bar ridges as the rotatable cross-bar rotates.

18. The wearable device of claim 14, wherein each rod is configured to be moved by the rotatable cross-bar based on friction between each rod and the rotatable cross-bar as the rotatable cross-bar rotates.

19. The wearable device of claim 14, wherein one or more physical components of each circuit system, of the set of circuit systems, is configured to break when over a threshold amount of pressure is placed on the one or more physical components.

* * * * *